United States Patent
Tamai et al.

(10) Patent No.: US 11,298,403 B2
(45) Date of Patent: Apr. 12, 2022

(54) THERAPEUTIC AGENT FOR INFLAMMATORY BOWEL DISEASE

(71) Applicants: StemRIM Inc., Osaka (JP); OSAKA UNIVERSITY, Osaka (JP)

(72) Inventors: Katsuto Tamai, Osaka (JP); Takashi Shimbo, Osaka (JP); Takehiko Yamazaki, Osaka (JP)

(73) Assignees: STEMRIM INC., Osaka (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 16/768,654

(22) PCT Filed: Nov. 30, 2018

(86) PCT No.: PCT/JP2018/044122
§ 371 (c)(1),
(2) Date: May 30, 2020

(87) PCT Pub. No.: WO2019/107530
PCT Pub. Date: Jun. 6, 2019

(65) Prior Publication Data
US 2020/0384074 A1 Dec. 10, 2020

Related U.S. Application Data

(60) Provisional application No. 62/593,310, filed on Dec. 1, 2017.

(30) Foreign Application Priority Data

Feb. 8, 2018 (JP) .................................. 2018-020686

(51) Int. Cl.
| | |
|---|---|
| *A61K 38/19* | (2006.01) |
| *A61K 38/17* | (2006.01) |
| *A61P 1/00* | (2006.01) |
| *A61P 1/04* | (2006.01) |
| *A61P 43/00* | (2006.01) |
| *C07K 14/47* | (2006.01) |

(52) U.S. Cl.
CPC ............ *A61K 38/1709* (2013.01); *A61P 1/04* (2018.01)

(58) Field of Classification Search
CPC .... A61K 38/1709; A61K 38/19; A61K 38/17; A61P 1/00; A61P 1/04; A61P 43/00; C07K 14/47
See application file for complete search history.

(56) References Cited

U.S. PATENT DOCUMENTS

| | | |
|---|---|---|
| 3,896,810 A | 7/1975 | Akiyama |
| 4,732,155 A | 3/1988 | Zetter et al. |
| 5,133,755 A | 7/1992 | Brekke |
| 5,661,127 A | 8/1997 | Bhatnagar et al. |
| 5,760,261 A | 6/1998 | Guttag |
| 5,851,986 A | 12/1998 | Takada et al. |
| 5,902,799 A | 5/1999 | Herrmann et al. |
| 6,905,874 B2 | 6/2005 | Berenson et al. |
| 7,220,723 B2 | 5/2007 | Tracey et al. |
| 7,288,250 B2 | 10/2007 | Newman et al. |
| 7,446,100 B2 | 11/2008 | Pilarski |
| 7,470,538 B2 | 12/2008 | Laughlin et al. |
| 7,585,504 B2 | 9/2009 | Wu et al. |
| 7,632,802 B2 | 12/2009 | Tessier et al. |
| 7,749,959 B2 | 7/2010 | Tracey et al. |
| 7,829,097 B2 | 11/2010 | Tsung et al. |
| 7,833,975 B2 | 11/2010 | Okazawa |
| 7,939,057 B2 | 5/2011 | Battista et al. |
| 8,114,668 B2 | 2/2012 | Stolen et al. |
| 8,119,121 B2 | 2/2012 | Fraser et al. |
| 8,551,470 B2 | 10/2013 | Son et al. |
| 8,673,580 B2 | 3/2014 | Tamai et al. |
| 9,623,078 B2 | 4/2017 | Tamai et al. |
| 9,688,733 B2 | 6/2017 | Tamai et al. |
| 9,919,010 B2 | 3/2018 | Tamai et al. |
| 10,364,276 B2 | 7/2019 | Tamai et al. |
| 10,393,762 B2 | 8/2019 | Fuhrmann et al. |
| 10,595,530 B2 | 3/2020 | Goodman et al. |
| 10,626,153 B2 | 4/2020 | Bianchi et al. |
| 2003/0003482 A1 | 1/2003 | Halle et al. |
| 2003/0060410 A1 | 3/2003 | Tracey et al. |
| 2004/0031072 A1 | 2/2004 | La Rosa et al. |

(Continued)

FOREIGN PATENT DOCUMENTS

| | | |
|---|---|---|
| AU | 2003228099 A1 | 1/2004 |
| AU | 2004203732 A1 | 7/2004 |

(Continued)

OTHER PUBLICATIONS

Overview of Inflammatory Bowel Disease from Merck Manual, pp. 1-3. Accessed Sep. 7, 2021. (Year: 2021).*
Crohn Disease from Merck Manual, pp. 1-7. Accessed Sep. 7, 2021. (Year: 2021).*
Ulcerative Colitis from Merck Manual, pp. 1-8. Accessed Sep. 7, 2021. (Year: 2021).*
Hu et al., "Role of high-mobility group box 1 protein in inflammatory bowel disease," Inflamm. Res., 2015, 64: 557-563. (Year: 2015).*

(Continued)

*Primary Examiner* — Julie Ha
(74) *Attorney, Agent, or Firm* — Saliwanchik, Lloyd & Eisenschenk

(57) ABSTRACT

The present inventors discovered that an HMGB1 fragment peptide having a specific amino acid sequence exhibits an effect of suppressing weight loss and an effect of suppressing shortening of the large intestine and mucosal damage in an animal model of inflammatory bowel diseases. Based on these findings, pharmaceutical compositions for the prevention and/or treatment of inflammatory bowel diseases, which comprise the HMGB1 fragment peptide having the specific amino acid sequence are provided.

6 Claims, 9 Drawing Sheets
Specification includes a Sequence Listing.

(56) References Cited

U.S. PATENT DOCUMENTS

| | | |
|---|---|---|
| 2004/0156851 A1 | 8/2004 | Newman |
| 2004/0191246 A1 | 9/2004 | Connelly et al. |
| 2004/0242481 A1 | 12/2004 | Bianchi et al. |
| 2004/0249448 A1 | 12/2004 | Gault |
| 2004/0265971 A1 | 12/2004 | Sato et al. |
| 2005/0014255 A1 | 1/2005 | Tang et al. |
| 2005/0101564 A1 | 5/2005 | Pilarski |
| 2006/0003312 A1 | 1/2006 | Blau et al. |
| 2006/0035851 A1 | 2/2006 | Bianchi et al. |
| 2006/0039896 A1 | 2/2006 | Kleinsek et al. |
| 2006/0069064 A1 | 3/2006 | Khaldoyanidi |
| 2006/0111287 A1 | 5/2006 | Bianchi |
| 2007/0154529 A1 | 7/2007 | Bullerdiek |
| 2007/0238663 A1 | 10/2007 | Capogrossi et al. |
| 2009/0053277 A1 | 2/2009 | Nagaya et al. |
| 2009/0062187 A1 | 3/2009 | Bianchi et al. |
| 2009/0202500 A1 | 8/2009 | Tamai et al. |
| 2010/0040608 A1 | 2/2010 | Wahren-Herlenius et al. |
| 2010/0280493 A1 | 11/2010 | Nayak |
| 2011/0097309 A1 | 4/2011 | Tamai et al. |
| 2012/0237504 A1 | 9/2012 | Brooks et al. |
| 2012/0251510 A1 | 10/2012 | Tamai et al. |
| 2015/0273017 A1* | 10/2015 | Tamai ............... C07K 14/4718 514/16.4 |
| 2018/0055886 A1 | 3/2018 | Tamai et al. |
| 2018/0072785 A1 | 3/2018 | Tamai et al. |
| 2019/0343924 A1 | 11/2019 | Tamai et al. |
| 2020/0038486 A1 | 2/2020 | Tamai et al. |
| 2020/0369736 A1 | 11/2020 | Tamai et al. |
| 2021/0024594 A1 | 1/2021 | Tamai et al. |
| 2021/0347839 A1 | 11/2021 | Tamai et al. |
| 2022/0009976 A1 | 1/2022 | Tamai et al. |

FOREIGN PATENT DOCUMENTS

| | | |
|---|---|---|
| CA | 2325226 A1 | 5/2001 |
| CA | 2512512 A1 | 7/2004 |
| CA | 2636788 A1 | 5/2008 |
| CN | 1193092 C | 3/2005 |
| CN | 1671742 A | 9/2005 |
| CN | 100447154 C | 12/2008 |
| CN | 101366728 A | 2/2009 |
| CN | 101374538 A | 2/2009 |
| CN | 102076350 A | 5/2011 |
| CN | 102443064 A | 5/2012 |
| CN | 102711777 B | 4/2015 |
| EP | 1114862 A2 | 7/2001 |
| EP | 1459759 A1 | 9/2004 |
| EP | 0791601 B1 | 4/2005 |
| EP | 2039367 A1 | 3/2009 |
| EP | 2055308 A1 | 6/2009 |
| EP | 2284255 A1 | 2/2011 |
| EP | 2301559 A1 | 3/2011 |
| EP | 2703487 A1 | 3/2014 |
| EP | 2913058 B1 | 12/2017 |
| EP | 3556378 A1 | 10/2019 |
| EP | 3719117 A1 | 10/2020 |
| JP | 3018313 B2 | 3/2000 |
| JP | 2003505506 A | 2/2003 |
| JP | 3421741 B2 | 6/2003 |
| JP | 2005508913 A | 4/2005 |
| JP | 2005512507 A | 5/2005 |
| JP | 2005537253 A | 12/2005 |
| JP | 2006510619 A | 3/2006 |
| JP | 2006517537 A | 7/2006 |
| JP | 2006523085 A | 10/2006 |
| JP | 2008507505 A | 3/2008 |
| JP | 2008511300 A | 4/2008 |
| JP | 2010503630 A | 2/2010 |
| JP | 4982739 B2 | 7/2012 |
| JP | 5134772 B2 | 1/2013 |
| JP | 5814549 B2 | 11/2015 |
| KR | 20090078304 A | 7/2009 |
| RU | 2005102593 A | 10/2005 |
| RU | 2410125 C2 | 1/2011 |
| RU | 2010148785 A | 6/2012 |
| RU | 2599448 C2 | 10/2016 |
| WO | 0108683 A1 | 2/2001 |
| WO | 02074337 A1 | 9/2002 |
| WO | 02088181 A2 | 11/2002 |
| WO | 02092004 A2 | 11/2002 |
| WO | 03026691 A2 | 4/2003 |
| WO | 03043651 A1 | 5/2003 |
| WO | 2004004763 A2 | 1/2004 |
| WO | 2004004770 A1 | 1/2004 |
| WO | 2004044001 A1 | 5/2004 |
| WO | 2004046345 A2 | 6/2004 |
| WO | 2004061456 A2 | 7/2004 |
| WO | 2005025604 A2 | 3/2005 |
| WO | 2005074984 A1 | 8/2005 |
| WO | 2005087797 A1 | 9/2005 |
| WO | 2006008779 A1 | 1/2006 |
| WO | 2006010628 A1 | 2/2006 |
| WO | 2006024547 A2 | 3/2006 |
| WO | 2006047820 A1 | 5/2006 |
| WO | 2006077614 A1 | 7/2006 |
| WO | 2006080434 A1 | 8/2006 |
| WO | 2006100651 A1 | 9/2006 |
| WO | 2006114805 A2 | 11/2006 |
| WO | 2007015546 A1 | 2/2007 |
| WO | 2007031100 A1 | 3/2007 |
| WO | 2007061762 A2 | 5/2007 |
| WO | 2007076200 A2 | 7/2007 |
| WO | 2007130725 A2 | 11/2007 |
| WO | 2008018641 A1 | 2/2008 |
| WO | 2008031612 A1 | 3/2008 |
| WO | 2008053892 A1 | 5/2008 |
| WO | 2008155659 A2 | 12/2008 |
| WO | 2009133939 A1 | 11/2009 |
| WO | 2009133940 A1 | 11/2009 |
| WO | 2009133943 A1 | 11/2009 |
| WO | 2011046570 A1 | 4/2011 |
| WO | 2011052668 A1 | 5/2011 |
| WO | 2012147470 A1 | 11/2012 |
| WO | 2014065347 A1 | 5/2014 |
| WO | 2014065348 A1 | 5/2014 |
| WO | 2014191364 A1 | 12/2014 |
| WO | 2016184795 A1 | 11/2016 |
| WO | 2018139562 A1 | 8/2018 |
| WO | 2018186480 A1 | 10/2018 |
| WO | 2019107566 A1 | 6/2019 |
| WO | 2019156137 A1 | 8/2019 |
| WO | 2020071519 A1 | 4/2020 |
| WO | 2020071520 A1 | 4/2020 |

OTHER PUBLICATIONS

Guillot, L., et al., "Response of Human Pulmonary Epithelial Cells to Lipopolysaccharide Involves Toll-like Receptor 4 (TLR4)-dependent Signaling Pathways." Journal of Biological Chemistry, Jan. 2004, 279(4): 2712-2718.

Guo, J., et al., "Monocyte Chemotactic Protein-1 Promotes the Myocardial Homing of Mesenchymal Stem Cells in Dilated Cardiomyopathy." International Journal of Molecular Sciences, 2013, 14: 8164-8178.

Harris, H.E., et al., "Alarmin(g) news about danger," EMBO Reports, 2006, 7(8): 774-778.

Harrison, C.A., et al., "Oxidation Regulates the Inflammatory Properties of the Murine S100 Protein S100A8." J. Biol. Chem., 1999, 274(13): 8561-8569.

Healthwise Staff, "Age-related Macular Degeneration," University of Michigan Health System, Aug. 2015, https:www.uofmhealth.org/health-library/hw176039.

He, Y.T., et al., "HMGB1 Ameliorates Inflammatory Bowel Disease by Inducing Circulating Mesenchymal Stem Cells." The 17th Congress of the Japanese Society for Regenerative Medicine, 2018, 34, Abstract.

Heil, M. et al., "An engineered heparin-binding form of VEGF-E (hbVEGF-E)," Angiogenesis, 2003, 6(3): 201-211.

(56) References Cited

OTHER PUBLICATIONS

Herrera, M.B. et al., "Exogenous mesenchymal stem cells localize to the kidney by means of CD44 following acute tubular injury," Kidney International, 2007, 72: 430-441.

Hiratsuka S. et al., "Tumour-mediated upregulation of chemoattractants and recruitment of myeloid cells predetermines lung metastasis," Natural Cell Biology, Dec. 2006, 8(12): 1369-1375.

HMGBiotech, "BoxA from HMGB1, human & mouse, LPS-free." HMGBiotech Srl, 2008, C.F. e P.IVA 04942740962, http://www.hmgbiotech.com/products.php?ID=91, ,accessed Jan. 27, 2017 from internet>.

HMGBiotech, "BoxA from HMGB1, human & mouse, LPS-free-Datasheet." HMGBiotech Srl, 2008, via Moretto da Brescia 25, 20133—Milano, Italy, http://www.hmgbiotech.com/upload/documenti/0515122144_boxa.

"HNRPK_HUMAN", NCBI_TaxID=9606, Accession No. P61978, Jun. 2004.

Hori, O et al., "The Receptor for Advanced Glycation End Products (RAGE) Is a Cellular Binding Site for Amphoterin," Journal of Biological Chemistry, 1995, 270(43): 25752-25761.

Hornef, M.W., et al., "Toll-like Receptor 4 Resides in the Golgi Apparatus and Colocalizes with Internalized Lipopolysaccharide in Intestinal Epithelial Cells." J. Exp. Med., 2002, 195(5): 559-570.

Hruby, V.J., "Designing Peptide Receptor Agonists and Antagonists." Nature Reviews Drug Discovery, 2002, 1: 847-858.

Huttunen, H.J. et al., "Receptor for Advanced Glycation End Products-binding COOH-terminal Motif of Amphoterin Inhibits Invasive Migration and Metastasis," Cancer Research, 2002, 62: 4805-4811.

Ichinose, K., et al., "Antiangiogenic Endostatin Peptide Ameliorates Renal Alterations in the Early Stage of a Type 1 Diabetic Nephropathy Model." Diabetes, Oct. 2005, 54(10): 2891-2903.

Instruction Manual of HiTrap chelating HP (Amersham Biosciences), 2003, pp. 1-6.

Ishikane, S., "Therapeutic application of allogenic fetal membrane-derived mesenchymal stem cells transplantation in regenerative medicine," Pharmaceutical Bulletin of Fukuoka University, Mar. 2011, 11(0): 17-25.

Ishikane, Shin, et al., "Development of multi-growth factor secreted fetal membrane-derived mesenchymal stem cell sheets." Grants-in-Aid for Scientific Research, 2014, pp. 1-6.

Jansen, J. et al., "Transplantation of hematopoietic stem cells from the peripheral blood," Journal of Cellular and Molecular Medicine, 2005, 9(1): 37-50.

Jayaraman, L. et al., "High mobility group protein-1 (HMG-1) is a unique activator of p53," Genes & Development, 1998, 12(4): 462-472.

Jiang, Y. et al., "Pluripotency of mesenchymal stem cells derived from adult marrow," Nature, 2002, 418(6893): 41-49.

Jiao, C. et al., "Researchers find nerve damage may precede diabetic retinopathy," EurekAlert! Science News, Apr. 2016, https://www.eurekalert.org/pub_releases/2016-04/uoih-rfv042616.php.

Jin, Y., "Isolating culture and induced differentiation of marrow mesenchyma stem cells," Principles and Protocols of Tissue Engineering, Jun. 2004, 277-278 (English translation attached).

Kaneda, et al., "Tissue repair mechanism by bone-marrow-derived stem cells." Experimental Mediciner, 2013, 31(5): 655-661.

Kassis, I. et al., "Isolation of mesenchymal stem cells from G-CSF mobilized human peripheral blood using fibrin microbeads," Bone Marrow Transplantation, 2006, 37(10): 967-976.

Kawabata, H. et al., "High Mobility Group Box 1 Is Upregulated After Spinal Cord Injury and Is Associated With Neuronal Cell Apoptosis," Spine, 2010, 35(11): 1109-1115.

Kern, S. et al., "Comparative Analysis of Mesenchymal Stem Cells from Bone Marrow, Umbilical Cord Blood, or Adipose Tissue," Stem Cells, 2006, 24(5): 1294-1301.

Kessler, M.W. et al., "Tissue Engineering and Cartilage," Organogenesis, Jan. 2008, 4(1): 28-32.

Kido, T., et al., "Abstract 15756: The Administration of High-morbidity Group Box 1 Fragment Prevents Deterioration of Cardiac Performance by Enhancement of Bone-marrow Mesenchymal Stem Cells Homing in the Delta-sarcoglycan-deficient Hamster." Circulation, Nov. 2017, 136(Suppl 1): Abstract.

Kikuchi, et al., "Systemic administration of HMGB1 improves bleomycin-induced skin fibrosis by locally accumulating bone marrow mesenchymal stem cells." Regenerative Medicine, Feb. 1, 2017, 16: 422.

Kikuchi, K. et al., "HMGB1 as a therapeutic target in spinal cord injury: A hypothesis for novel therapy development (Review)," Experimental and Therapeutic Medicine, 2011, 2: 767-770.

Kim, S. et al., "Skin Regeneration Using Keratinocytes and Dermal Fibroblasts Cultured on Biodegradable Microspherical Polymer Scaffolds," Journal of Biomedical Materials Research Part B: Applied Biomaterials, 2005, 75(2): 369-377.

Kirov, S.A. et al., "In Vivo 2-Photon Microscopy Reveals G-CSF Enhanced Mobilization and Targeting of Neo-Endogenous Bone Marrow Stromal Cells to Stroke Injury Sites," Stroke, Apr. 2009, 40(4): 1-2, e133, Abstract No. 107.

Kitahara, T. et al., "High-Mobility Group Box 1 Restores Cardiac Function After Myocardial Infarcation in Transgenic Mice," Cardiovascular Research, European Society of Cardiology, Oct. 1, 2008, 80: 40-46.

Koc, O. et al., "Mesenchymal Stem Cells: Heading into the Clinic," Bone Marrow Transplantation, 2001, 27(3): 235-239.

Kohno, T. et al., "High Mobility Group Box 1 Protein is Associated With Post-Infarction Healing Process and Left Ventricular Remodeling," Circ. J., 2008, 72, Supplement 1, P J-004: 510-511.

Kokkola, R., et al., "RAGE is the Major Receptor for the Proinflammatory Activity of HMGB1 in Rodent Macrophages." Scandinavian Journal of Immunology, 2005, 61: 1-9.

Komurasaki, Y., et al., "555 Systemic HMGB1 Administration Ameliorated Bleomycin-Induced Skin Fibrosis by Promoting Accumulation of Bone Marrow-Derived Mesenchymal Stem Cells to the Lesion." Journal of Investigative Dermatology, 2016, 136(9): S255.

Komurasaki, Y., et al., "HMGB1 Ameliorates Bleomycin-Induced Skin Fibrosis by Promoting Accumulation of Mesenchymal Stem Cells to the Lesion." The 48th Annual Meeting of the Japanese Society of Matrix Biology and Medicine, 2016: 78.

Koren-Morag, N., et al., "White Blood Cell Count and the Incidence of Ischemic Stroke in Coronary Heart Disease Patients." The American Journal of Medicine, 2005, 118: 1004-1009.

Laflamme, M. et al., "Regenerating the heart," Nature Biotechnology, Jul. 2005, 23(7): 845-856.

Lanza, R. et al., "Essentials of Stem Cell Biology—Chapter 27, Mesenchymal Stem Cells," Elsevier Academic Press, 2006, pp. 205-210.

La Rosa, T.J. et al., "Glycine max protein Seq ID No. 211221," Geneseq Accession No. AFQ20044, 2007.

Lemp, M.A., et al., "The Definition and Classification of Dry Eye Disease: Report of the Definition and Classification Subcommittee of the International Dry Eye Workshop (2007)." The Ocular Surface, Apr. 2007, 5(2): 75-92.

Li, S. et al., "Millennium Review, Nonviral gene therapy: promises and challenges," Gene Ther., 2000, 7: 31-34.

Li, Z. et al., "Heat-Shock Proteins," Current Protocols in Immunology, 2003, Supplement 58, A.IT.1-A.IT.6.

Li, Y. et al., "Advancement of Human Multiply, Sex health and Reproductive Medical Science," Peking University Medical Press, Mar. 2007, 1st Edition, pp. 270-271.

Li, L., et al., "Emerging Role of HMGB 1 in Fibrotic Diseases." Journal of Cellular and Molecular Medicine, 2014, 18(12): 2331-2339.

Pusterla, T. et al., "High mobility group B2 is secreted by myeloid cells and has mitogenic and chemoattractant activities similar to high mobility group B1," Autoimmunity, 2009, 42(4): 308-310.

Quertainmont, R. et al., "Mesenchymal Stem Cell Graft Improves Recovery after Spinal Cord Injury in Adult Rats through Neurotrophic and Pro-Angiogenic Actions," PLoS One, Jun. 2012, 7(6): 1-15, e39500.

Racanelli, V., et al., "The Liver as an Immunological Organ." Hepatology, 2006, 43(2): Suppl. 1—S54-S62.

(56) References Cited

OTHER PUBLICATIONS

Rahimi-Movaghar, V. et al., "Effect of Decompression on Complete Spinal Cord Injury in Rats," International Journal of Neuroscience, 2008, 118: 1359-1373.

Raicevic, G. et al., "Inflammation modifies the pattern and the function of Toll-like receptors expressed by human mesenchymal stromal cells," Human Immunology, 2010, 71(3): 235-244.

Raucci, A., et al., "The Janus Face of HMGB1 in Heart Disease: A Necessary Update." Cellular and Molecular Life Sciences, 2019, 76: 211-229.

Robinson, M.J. et al., "The S100 Family Heterodimer, MRP-8/14, Binds with High Affinity to Heparin and Heparan Sulfate Glycosaminoglycans on Endothelial Cells," Journal of Biological Chemistry, 2002, 277(5): 3658-3665.

Ross, M.H., et al., "Histology: a Text and Atlas: With Correlated Cell and Molecular Biology." Lippincott Williams & Wilkins, 2018.

Ryckman, S. et al., "Proinflammatory Activities of S100: Proteins S100A8, S100A9, and S100A8/A9 Induce Neutrophil Chemotaxis and Adhesion." J. Immunol., 2003, 170(6): 3233-3242.

Santamaria-Kisiel, L. et al., "Calcium-dependent and -independent interactions of the S100 protein family." Biochem. J., 2006, 396: 201-214.

Sasaki, M. et al., "Mesenchymal Stem Cells Are Recruited into Wounded Skin and Contribute to Wound Repair by Transdifferentiation into Multiple Skin Cell Type." The Journal of Immunology, Feb. 15, 2008, 180(4): 2581-2587.

Saver, J.L., "Time Is Brain-Quantified." Stroke, Jan. 2006, 37: 263-266.

Schaffer, M. R. et al., "Wound Fluid Inhibits Wound Fibroblast Nitric Oxide Synthesis." Journal of Surgical Research, 2004, 122(1): 43-48.

Schon, M. P., Boehncke, W. H., "Medical Progress: Psoriasis." The New England Journal of Medicine, May 2005, 352(18): 1899-1912.

Scoote, M., et al., "Chapter 19—Pathophysiology of Heart Failure." Essential Cardiology: Principles and Practice, 2006, 2nd Edition, Chapter 19, pp. 347-369.

Seffernick, J. L., "Melamine Deaminase and Atrazine Chlorohydrolase: 98 Percent Identical but Functionally Different." Journal of Bacteriology, 2001, 183(8): 2405-2410.

Selected cardiac diagnoses and ICD-10 codes, 2021, 1 page.

Seong, YS., Matzinger, P., "Hydrophobicity: an ancient damage-associated molecular pattern that initiates innate immune responses." Nature Reviews: Immunology, Jun. 2004, 4(6): 469-478.

Shibata, F. et al., "Fibroblast growth-stimulating activity of S100A9 (MRP-14)." Eur. J. Biochem., Feb. 2004, 271(11): 2137-2143.

Shing, Y et al., "Heparin Affinity: Purification of a Tumor-Derived Capillary Endothelial Cell Growth Factor." Science, Mar. 23, 1984, 223: 1296-1299.

Simard, A. R., et al., "Bone Marrow-Derived Microglia Play a Critical Role in Restricting Senile Plaque Formation in Alzheimer's Disease." Neuron, 2006, 49(4): 489-502.

Slater, M. et al., "Endometriotic cells exhibit metaplastic change and oxidative DNA damage as well as decreased function, compared to normal endometrium." Journal of Molecular Histology, 2005, 36(4): 257-263.

Somia, N., Verma, I. M., "Reviews, Gene Therapy: Trials and Tribulations." Nature Reviews: Genetics, Nov. 2000, 1(2): 91-99.

Soo, E.T.L. et al., "Heat Shock Proteins as Novel Therapeutic Targets in Cancer." in vivo, 2008, 22(3): 311-315.

SP16H_HUMAN, Accession No. Q9Y5B9, Jul. 2006.

Straino, S. et al., "High-Mobility Group Box 1 Protein in Human and Murine Skin: Involvement in Wound Healing." Journal of Investigative Dermatology, Jan. 2008, 128: 1545-1553.

Sun, S. et al., "Isolation of Mouse Marrow Mesenchymal Progenitors by a Novel and Reliable Method." Stem Cells, 2003, 21(5): 527-535.

Tagami, K. et al., "Elevation of serum high-mobility group box 1 protein during granulocyte colony-stimulating factorinduced peripheral blood stem cell mobilisation." British Journal of Haematology, 2006, 135(4): 567-569.

Tagliafico, E. et al., "TGFB/BMP activate the smooth muscle/bone differentiation programs in mesoangioblasts." Journal of Cell Science, Apr. 2004, 117(19): 4377-4388.

Takahashi, Kunihiko, et al., "Modulated Inflammation by Injection of High-Mobility Group Box 1 Recovers Post-Infarction Chronically Failing Heart." Circulation, Sep. 2008, 118(14 Suppl): S106-S114.

Takahashi, K. et al., "Effects of HMGB1 on PostInfarction Chronic Heart Failure—Novel Mechanism Regarding Therapeutic Effects of Cell Therapy." Supplement, 2011, 27 I-E-19:S189.

Takami, Y. et al., "Synergistic induction of hepatocyte growth factor in human skin fibroblasts by the inflammatory cytokines interleukin-1 and interferon-y." Biochemical and Biophysical Research Communications, 2005, 327: 212-217.

Takeishi, Yasuchika et al., "Importance of Inflammation and Immune Response in Heart Failure—Toll-Like Receptor-Mediated Signaling Pathway and Ventricular Remodeling After Myocardial Infarction." Journal of Clinical and Experimental Medicine, Jan. 30, 2010, 232(5):378-385.

Tamai, K., "Development of Regeneration-Inducing Medicine Utilizing Molecular Mechanism for in vivo tissue Regeneration by Circulating Mesenchymal Stem Cells." Bio Clinica, 2016, 31(10): 1042-1046.

Tamai, K. et al., "PDGFRα-positive cells in bone marrow are mobilized by high mobility group box 1 (HMGB1) to regenerate inured epithelia," Proceedings of the National Academy of Sciences, 2011, 108(16): 6609-6614.

Tamai, K. et al., "Development and Outlook of Internal Regeneration-Inducing Pharmaceuticals that use in vivo Bone Marrow Mesenchymal Stem / Progenitor Cell-Mobilizing Factors," Gene & Medicine Mook, Jul. 22, 2012, pp. 207-212.

Tamai et al., "Nihon Hiuka Gakkai Zasshi," Japanese Journal of Dermatology, 2008, 118(4): 645 (#EL28-4) (translated English abstract attached, titled "New Wave of Wound Healing").

Tamai, K. et al., U.S. Appl. No. 11/997,475, "Mesenchymal Stem Cell Inducer, Tissue Regeneration Promoter and Method of Preparing Mesenchymal Stem Cell." filed Jan. 31, 2008.

Tamai, K. et al., U.S. Appl. No. 15/517,967, "Agents for Promoting Tissue Regeneration by Recruiting Bone Marrow Mesenchymal Stem Cells and/or Pluripotent Stem Cells into Blood ." filed Nov. 3, 2021.

Tamilselvi, E., et al., "Association of Disease Severity with IL-1 Levels in Methotrexate-Treated Psoriasis Patients." Scandinavian Journal of Immunology, 2013, 78: 545-553.

Tang, D. et al., "High-Mobility Group Box 1, Oxidative Stress, and Disease." Antioxidants & Redox Signaling, 2011, 14(7): 1315-1335.

Tang, L., Eaton, J. W., "Fibrin(ogen) Mediates Acute Inflammatory Responses to Biomaterials." J. Exp. Med., Dec. 1993, 178: 2147-2156.

Tao, A., et al., "Cardiomyocyte-Fibroblast Interaction Contributes to Diabetic Cardiomyopathy in Mice: Role of HMGB1/TLR4/IL-33 Axis." Biochimica et Biophysica Ada, 2015, 1852: 2075-2085.

Tatsumi, R. et al., "HGF/SF Is Present in Normal Adult Skeletal Muscle and Is Capable of Activating Satellite Cells," Developmental Biology, 1998, 194: 114-128.

Telusma, G. et al., "Dendritic cell activating peptides induce distinct cytokine profiles," International Immunology, 2006, 18(11): 1563-1573.

Teoh, N., et al., "Low-Dose TNF-Alpha Protects Against Hepatic Ischemia-Reperfusion Injury in Mice: Implications for Preconditioning." Hepatology, 2003, 37(1): 118-128.

Thorey, I.S. et al., "The Ca2+-binding Proteins S100A8 and S100A9 Are Encoded by Novel Injury-regulated Genes*," Journal of Biological Chemistry, 2001, 276(38): 35818-35825.

Tokuriki, N., et al., "Stability Effects of Mutations and Protein Evolvability." Current Opinion in Structural Biology, 2009, 19: 596-604.

Tsung, A., et al., "Hepatic Ischemia/Reperfusion Injury Involves Functional TLR4 Signaling in Nonparenchymal Cells." The Journal of Immunology, 2005, 175(11): 7661-7668.

(56) References Cited

OTHER PUBLICATIONS

Limana, F. et al., "Exogenous High-Mobility Group Box 1 Protein Induces Myocardial Regeneration After Infarction via Enhanced Cardiac C-Kit+ Cell Proliferation and Differentiation," Circulation Research, 2005, 97(8): e73-83.

Limana, F., et al., "HMGB1 Attenuates Cardiac Remodelling in the Failing Heart via Enhanced Cardiac Regeneration and miR-206-Mediated Inhibition of TIMP-3." PLoS One, 2011, 6(6): e19845, pp. 1-11.

Lin, S. et al., "The isolation of novel mesenchymal stromal cell chemotactic factors from the conditioned medium of tumor cells." Experimental Cell Research, 2008, 314(17): 3107-3117.

Liotta, F. et al., "Toll-Like Receptors 3 and 4 Are Expressed by Hunan Bone Marrow-Derived Mesenchymal Stem Cells and Can Inhibit Their T-Cell Modulatory Activity by Impairing Notch Signaling." Stem Cells, 2008, 26(1): 279-289.

Liu, K.et al., "Human Placental Extract Stimulates Liver Regeneration in Rats," Biological and Pharmaceutical Bulletin, 1998, 21(1): 44-49.

Lonza BenchGuides_Poietics hMSC Human Mesenchymal Stem Cells and Media (Document # TS-PT-212-7 Apr. 2008), 2008, Walkersville, MD, USA.

Lund, L., et al., "The Registry of the International Society for Heart and Lung Transplantation: Thirty-Third Adult Heart Transplantation Report—2016; Focus Theme: Primary Diagnostic Indications for Transplant." The Journal of Heart and Lung Transplantation, 2016, 35(10): 1158-1169.

Mansbridge, J. et al., "Skin Tissue Engineering," J. Biomater, Sci. Polymer, Ed., Aug. 1, 2008, 19(8): 955-968.

Maron, B.J., et al., "Contemporary Definitions and Classification of the Cardiomyopathies—An American Heart Association Scientific Statement from the Council on Clinical Cardiology, Heart Failure and Transplantation Committee; Quality of Care and Outcomes Research and Functional Genomics and Translational Biology Interdisciplinary Working Groups; and Council on Epidemiology and Prevention." Circulation, 2006, 113: 1807-1816.

Martin-Murphy, B.V. et al., "The Role of Damage Associated Molecular Pattern Molecules in Acetaminophen-Induced Liver Injury in Mice," Toxicol Lett, Feb. 2010, 192(3): 1-20.

Maruyama, I., "Inflammation and HMGB1/RAGE system," Kekkan Igaku, 2005, 6(5): 519-525 (English translation attached).

Matsumoto, K., et al., "Up-Regulation of Hepatocyte Growth Factor Gene Expression by Inerleukin-1 in Human Skin Fibrosis," Biochemical and Biophysical Research Communications, 1992, 188(1): 235-243.

Meng, E. et al., "HMGB1 induces migration of human bone marrow-derived mesenchymal stem cells," Bulletin of the Academy of Militaryt Medical Sciences, 2006, 30(3): 213-216 (English translation attached).

Meng, E. et al., "High Mobility Group Box 1 Protein Inhibits the Proliferation of Human Mesenchymal Stem Cells and Promotes Their Migration and Differentiation along Osteoblastic Pathway," Stem Cells and Development, 2008, 17(4): 805-814.

Merenmies, J. et al., "30-kDa Heparin-binding Protein of Brain (Amphoterin) Involved in Neurite Outgrowth," Journal of Biological Chemistry 1991, 266(25): 16722-16729.

Mistry, A.R. et al., "Recombinant HMG1 Protein Produced in Pichia pastoris: A Nonviral Gene Delivery Agent," Biotechniques, 1997, 22(4): 718-729.

Mori, T. et al., "Stem Cells/ES cells—Mesenchymal Stem Cells—Human Bone Marrow Derived Mesenchymal Stem Cells," Saisei lryou—Regenerative Medicine, 2005, 4(3): 421-429, 351.

Morosetti, R. et al., "MyoD expression restores defective myogenic differentiation of human mesoangioblasts from inclusion-body myositis muscle," PNAS, Nov. 7, 2006, 103(45): 16995-17000.

Mouse care guidance from the Institutional Animal Care and Use Committee at University of California, San Francisco; iacuc.ucsf.edu/Policies/BloodCollectionMice.doc; accessed May 15, 2014.

Muhamed, J. et al., "Phenotypic Modulation of Cell Types around Implanted Polyethylene Terephthalate Fabric in Rabbit Muscle." Toxicologic Pathology, 2013, 41: 497-507.

Muhammad, S. et al., "The HMGB1 Receptor RAGE Mediates Ischemic Brain Damage." The Journal of Neuroscience, Nov. 12, 2008, 28(46): 12023-12031.

Müller, S. et al., "The double life of HMGB1 chromatin protein: architectural factor and extracellular signal," EMBO Journal, 2001, 20(16): 4337-4340.

Musumeci, D., et al., "An overview on HMGB1 inhibitors as potential therapeutic agents in HMGB1-related pathologies." Pharmacology & Therapeutics, 2014, 141: 347-357.

Nakajima et al., "Dynamics and Role of High Mobility Group Box-1 (HMGB-1) in Injured Spinal Cord," Nihon Seikei Geka Gakkai Zasshi (J. Jpn. Orthop. Assoc.), 2010, 84(8): S1050.

Nakamura, K. et al., "p38 Mitogen-Activated Protein Kinase Functionally Contributes to Chondrogenesis Induced by Growth/Differentiation Factor-5 in ATDC5 Cells," Experimental Cell Research, 1999, 250(2): 351-363.

Nakanishi, S., et al., "Membrane Potential-Regulated Ca2+ Signalling in Development and Maturation of Mammalian Cerebellar Granule Cells." J. Physiol., 2006, 575(2): 389-395.

Narumi, T., et al., "High-Mobility Group Box 1—Mediated Heat Shock Protein Beta 1 Expression Attenuates Mitochondrial Dysfunction and Apoptosis." Journal of Molecular and Cellular Cardiology, 2015, 82: 1-12.

Narumi, T., et al., "High-mobility Group Box 1 Attenuates Mitochondrial Dysfunction and Apoptosis via Heat Shock Protein Beta 1 Induction in Doxorubicin-induced Cardiomyopathy." Bulletin of Yamagata University (Medical Science ), 2015, 33(2): 126-127. http://www.lib.yamagata-u.ac.jp/alllib/elib/kiyou/kiyoum/kiyoum-33-2/image/kiyoum-33-2-125to131.pdf.

NCBI, "Old myocardial infarction." MedGen UID: 57612, retrieved from Internet Jan. 19, 2022, <https://www.ncbi.nlm.nih.gov/medgen/57612>.

Nickoloff, B. J., et al., "Recent Insights into the Immunopathogenesis of Psoriasis Provide new Therapeutic Opportunities." J. Clin. Invest., 2004, 113(12): 1664-1675.

O'Callaghan, A., et al., "HMGB1 as a Key Mediator of Tissue Response to Injury: Roles in Inflammation and Tissue Repair." European Surgery, 2006, 38: 283-292.

Opitz, C.E. et al., "Toll-Like Receptor Engagement Enhances the Immunosuppressive Properties of Human Bone Marrow-Derived Mesenchymal Stem Cells by Inducing Indoleamine-2, 3-dioxygenase-1 via Interferon-β and Protein Kinase R," Stem Cells, 2009, 27(4): 909-919.

Otsuru, S. et al., "BMP-2 mobilizes robust bone marrow mesenchymal progenitor cells to the circulating blood in bone regeneration," The 28th Meeting of the Molecular Biology Society of Japan, 2005, 733(3P-1012) (translated English abstract attached).

Ozaki, Y. et al., "Comprehensive Analysis of Chemotactic Factors for Bone Marrow Mesenchymal Stem Cells," Stem Cells and Development, 2007, 16(1): 119-129.

PA2G4_HUMAN, Accession No. Q9UQ80, Apr. 2001.

Palumbo, R. et al., "Extracellular HMGB1, a signal of tissue damage, induces mesoangioblast migration and proliferation," The Journal of Cell Biology, 2004, 164(3): 441-449.

Palumbo, R. et al., "High mobility group box 1 protein, a cue for stem cell recruitment," Biochemical Pharmacology, 2004, 68(6): 1165-1170.

Palumbo, R. et al., "Cells migrating to sites of tissue damage in response to the danger signal HMGB1 require NF-kB activation," Journal of Cell Biology, 2007, 179(1): 33-40.

Pandya, N.M., et al., "Angiogenesis—A New Target for Future Therapy." Vascular Pharmacology, 2006, 44: 265-274.

Panepucci, R.A. et al., "Abstract # 4427: Comparison of Gene Expression of Mesenchymal Stem Cells from the Umbilical Cord and from the Bone Marrow," Blood, Nov. 2003, 16(102): Abstract.

Panepucci, R. A. et al., "Comparison of Gene Expression of Umbilical Cord Vein and Bone Marrow-Derived Mesenchymal Stem Cells." Stem Cells, Dec. 2004, 22(7): 1263-1278.

Pankov, R. et al., Fibronectin at a glance, J. Cell Sci., Oct. 2002, 115(20): 3861-3863.

(56) References Cited

OTHER PUBLICATIONS

Park, J., et al., "Involvement of Toll-Like Receptors 2 and 4 in Cellular Activation by High Mobility Group Box 1 Protein." Journal of Biological Chemistry, 2004, 279(9): 7370-7377.

Paul, S.R. et al., "Stromal Cell-Associated Hematopoiesis: Immortalization and Characterization of a Primate Bone Marrow-Derived Stromal Cell Line," Blood, 1991, 77(8): 1723-1733.

Pevsner-Fischer, M. et al., "Toll-like receptors and their ligands control mesenchymal stem cell functions," Blood, 2007, 109(4): 1422-1432.

PFD5_HUMAN, Accession No. Q99471, Nov. 1997.

Pittenger, M. et al., "Multilineage Potential of Adult Human Mesenchymal Stem Cells," Science, 1999, 284(5411): 143-147.

PM_HUMAN, Accession No. P06748, Jan. 1988.

Popovic, K. et al., "Increased Expression of the Novel Proinflammatory Cytokine High Mobility Group Box Chromosomal Protein 1 in Skin Lesions of Patients With Lupus Erythematosus," Arthritis & Rheumatism, 2005, 52(11): 3639-3645.

PRS6A_HUMAN, Accession No. P17980, Nov. 1990.

Türker, S. et al., "Nasal route and drug delivery systems," Pharmacy World and Science, 2004, 26: 137-142.

Uchida et al., "Nihon Seikei Geka Gakkai Zasshi," The Journal of Japanese Orthopaedic Surgical Society, 2005, 79(8): S832, 1-P6-6. (English translation attached, titled "The chemotactic activity of PDGF-bb BMP-2, and FGF-2 towards committed and uncommitted mesenchymal stem cells").

Ueta, M., et al., "Intracellularly Expressed TLR2s and TLR4s Contribution to an Immunosilent Environment at the Ocular Mucosal Epithelium." The Journal of Immunology, 2004, 173(5): 3337-3347.

Ulloa, L. et al., "High-mobility group box 1 (HMGB1) protein: Friend and foe," Cytokine & Growth Factor Reviews, 2006, 17: 189-201.

Uronen-Hansson, H., et al., "Toll-like Receptor 2 (TLR2) and TLR4 are Present Inside Human Dendritic Cells, Associated with Microtubules and the Golgi Apparatus but are not Detectable on the Cell Surface: Integrity of Microtubules is Required for Interleukin-12 Production in Response to Internalized Bacteria." Immunology, 2004, 111: 173-178.

User Manual for StemCell Technologies, "Enumeration, Expansion, and Differentiation of Human Mesenchymal Progenitor Cells Using MesenCult." StemCell Technologies, Oct. 2007, Version 2.2.0.

Vandal, K. et al., "Blockade of S100A8 and S100A9 Suppresses Neutrophil Migration in Response to Lipopolysaccharide." The Journal of Immunology, Sep. 1, 2003, 171(5): 2602-2609.

Venereau, E. et al., "Mutually exclusive redox forms of HMGB1 promote cell recruitment or proinflammatory cytokine release." The Journal of Experimental Medicine, 2012, 209(9): 1519-1528.

Wang, H.L. et al., "High mobility group protein B1 and the research progress of its biological effect," Journal of Chinese Modern Surgery, 2006, 3(22): 1806-1809 (English translation attached).

Wang, H. et al., "HMG-1 as a Late Mediator of Endotoxin Lethality in Mice," Science, 1999, 285(5425): 248-251.

Wang, L. et al., "Ischemic cerebral tissue and MCP-1 enhance rat bone marrow stromal cell migration in interface culture," Experimental Hematology, 2002, 30: 831-836.

Wang, H. et al., "Kansaibou no riron to gijutu," Science Press, Mar. 2005, 5: 58-61 (English translation attached, titled "Theories and Technologies for Stem Cells").

Wang, H.Y., et al., "Rate of Evolution in Brain-Expressed Genes in Humans and Other Primates." PLoS Biol., Feb. 2007, 5(2): e13, pp. 0335-0342.

Wang, W. et al., "Intravenous administration of bone marrow mesenchymal stromal cells is safe for the lung in a chronic myocardial infarction model," Regen Med, Mar. 2011, 6(2): 179-190.

Wang, F.-C., et al., "Overexpression of HMGB1 A-box reduced lipopolysaccharide-induced intestinal inflammation via HMGB1/TLR4 signaling in vitro." World J Gastroenterol, Jul. 7, 2015, 21(25): 7764-7776.

Wang, Y., "Biology of hematopoietic stem cell and the research method therof," Science Press, Mar. 2007, 1st Edition, pp. 56-58.

Watanabe, T., et al., "The Role of HMGB-1 on the Development of Necrosis During Hepatic Ischemia and Hepatic Ischemia/Reperfusion Injury in Mice." Journal of Surgical Research, 2005, 124: 59-66.

Weintraub, R.G., et al., "Dilated cardiomyopathy." Lancet, 2017, 390(10092): 400-414.

Wexler, S. et al., "Adult Bone Marrow is a Rich Source of Human Mesenchymal 'Stem' Cells but Umbilical Cord and Mobilized Adult Blood are Not," British Journal of Haematology, 2003, 121(2): 368-374.

Whisstock, J.C., et al., "Prediction of Protein Function from Protein Sequence and Structure." Quarterly Reviews of Biophysics, 2003, 36(3): 307-340.

Witkowski, A., et al., "Conversion of a β-Ketoacyl Synthase to a Malonyl Decarboxylase by Replacement of the Active-Site Cysteine with Glutamine." Biochemistry, 1999, 38: 11643-11650.

Wolf, G. et al., "From the Periphery of the Glomerular Capillary Wall Toward the Center of Disease," Diabetes, Jun. 2005, 54(6): 1626-1634.

Woodbury, D. et al., "Adult Rat and Human Bone Marrow Stromal Cells Differentiate into Neurons," Journal of Neuroscience Research, Aug. 15, 2000, 61(4): 364-370.

Wu, Y. et al., "Mesenchymal Stem Cells Enhance Wound Healing Through Differentiation and Angiogenesis," Stem Cells, 2007, 25(10): 2648-2659.

Yamada, T. et al., "Regulation of osteoclast development by Notch signaling directed to osteoclast precursors and through stromal cells," Blood, Mar. 2003, 101(6): 2227-2234.

Yamaoka, S., et al., "1043 Systemic delivery of HMGB1 peptide ameliorates imiquimod-induced psoriasis-like dermatitis." Journal of Investigative Dermatology, 2018, 138(5): S177.

Yang, H., et al., "Reversing established sepsis with antagonists of endogenous high-mobility group box 1." Proceedings of the National Academy of Sciences, 2004, 101(1): 296-301.

Yang, D. et al., "High mobility group box-1 protein induces the migration and activation of human dendritic cells and acts as an alarmin," Journal of Leukocyte Biology, 2007, 81(1): 59-66.

Yang, S., et al., "Does Pretreatment of Bone Marrow Mesenchymal Stern Cells with 5-Azacytidine or Double Intravenous Infusion Improve Their Therapeutic Potential for Dilated Cardiomyopathy?" Medical Science Monitor Basic Research, 2013, 19: 20-31.

YBOX1_HUMAN, Accession No. P67809, Oct. 2004.

Youn, J.H. et al., "High Mobility Group Box 1 Protein Binding to Lipopolysaccharide Facilitates Transfer of Lipopolysaccharide to CD14 and Enhances Lipoplysaccharide-Mediated TNF-α Production in Human Monocytes," Journal of Immunology, 2008, 180(7): 5067-5074.

Yuan, Y. et al., "Differentiation of Mesenchymal Stem Cells in Cardiomyogenic Cells Under the Induction of Myocardial Cell Lysate," Chinese Journal of Cardiology, 2005, 33(2): 170-173.

Yu, Q., et al., "Impact of Repeated Intravenous Bone Marrow Mesenchymal Stem Cells Infusion on Myocardial Collagen Network Remodeling in a Rat Model of Doxorubicin-Induced Dilated Cardiomyopathy." Molecular and Cellular Biochemistry, 2014: 279-285.

Zheng, X., et al., "Adeno-associated virus-mediated colonic secretory expression of HMGB1 A box attenuates experimental colitis in mice." J Gene Med, 2016, 18(10): 261-272.

Zhou, X., et al., "Section 2 The translation process of genetic information." Molecular Genetics, 1992, pp. 141-143.

Zhou, X. et al., "Exogenous High-Mobility Group Box 1 Protein Injection Improves Cardiac Function after Myocardial Infarction: Involvement of Wnt Signaling Activation," Journal of Biomedicine and Biotechnology, 2012, vol. 2012, Article ID 743879, pp. 1-5.

Zhou, Y.-H., et al., "High mobility group box 1 protein attenuates myocardial ischemia reperfusion injury via inhibition of the p38 mitogen-activated protein kinase signaling pathway." Experimental and Therapeutic Medicine, 2017, 14: 1582-1588.

Alden, T. D., et al., "In Vivo Endochondral Bone Formation Using a Bone Morphogenetic Protein 2 Adenoviral Vector." Human Gene Therapy, Sep. 1999, 10(13): 2245-2253.

Andersson, U. et al., "HMGB1 as a DNA-binding cytokine." Journal of Leukocyte Biology, 2002, 72: 1084-1091.

(56) References Cited

OTHER PUBLICATIONS

Arminan, A. et al., "Mesenchymal Stem Cells Provide Better Results Than Hematopoietic Precursors for the Treatment of Myocardial Infarction." Journal of the American College of Cardiology, 2010, 55(20): 2244-2253.

Arnau, J. et al., "Current Strategies for the use of Affinity Tags and Tag Removal for the Purification of Recombinant Proteins." Protein Expression and Purification, 2006, 48: 1-13.

Asch, F.M., et al., "Lack of sensitivity of the electrocardiogram for detection of old myocardial infarction: A cardiac magnetic resonance imaging study." American Heart Journal, Oct. 2006, 152(4): 742-748.

Ball, S.G., et al., "Mesenchymal stem cells and neovascularization: role of platelet-derived growth factor receptors." J. Cell. Mo. Med., 2007, 11(5): 1012-1030.

Basso, D. M. et al., "Basso Mouse Scale for Locomotion Detects Differences in Recovery after Spinal Cord Injury in Five Common Mouse Strains." Journal of Neurotrauma, 2006, 23(5): 635-659.

Berry, M. F. et al., "Mesenchymal stem cell injection after myocardial infarction improves myocardial compliance." Am. J. Physiol. Heart Circ. Physiol., Jun. 2006, 290(6): H2196-H2203.

Bianchi, M. E., "High mobility group 1 protein (HMGB1) N-terminal peptide." Geneseq Accession No. ADO80180, Aug. 12, 2004.

Bianchi, M. E. et al., "The DNA binding site of HMG1 protein is composed of two similar segments (HMG boxes), both of which have counterparts in other eukaryotic regulatory proteins." The EMBO Journal, Mar. 1992, 11(3): 1055-1063.

Bittira, B. et al., "Mobilization and homing of bone marrow stromal cells in myocardial infarction." European Journal of Cardio-thoracic Surgery, 2003, 24(3): 393-398.

Blain, A.M., et al., "δ-Sarcoglycan-deficient muscular dystrophy: from discovery to therapeutic approaches." Skeletal Muscle, 2011, 1(13): 1-13.

Brunner, S., et al., "Erythropoientin Administration After Myocardial Infarction in Mice Attenuates Ischemic Cardiomyopathy Associated with Enhanced Homing of Bone Marrow-Derived Progenitor Cells via the CXCR-4/SDF-1 Axis." The FASEB Journal, 2009, 23: 351-361.

"BTF3_HUMAN", NCBI_TaxID=9606, Accession No. P20290, Feb. 1991.

Bustin, M., "Regulation of DNA-Dependent Activities by the Functional Motifs of the High-Mobility-Group Chromosomal Proteins." Mol. Cell. Biol., 1999, 19(8): 5237-5246.

Cairo, M. S. "Results of a Phase I/II Trial of Recombinant Human Granulocyte-Macrophage Colony-Stimulating Factor in Very Low Birthweight Neonates: Significant Induction of Circulatory Neutrophils, Monocytes, Platelets, and Bone Marrow Neutrophils." Blood, 1995, 86(7): 2509-2515.

"Cardiomegaly" Merriam Webster, 2015 archived page, accessed via Wayback Machine [online] [accessed at https://web.archive.org/web/20150107154504/https://www.merriam-webster.com/medical/cardiomegaly on May 21, 2020]. (Year: 2015).

"Cardiomyopathy: Symptoms, diagnosis and treatment." Harvard Health Publishing Harvard Medical School, Dec. 29, 2014.

Castro, R. F. et al., "Failure of Bone Marrow Cells to Transdifferentiate into Neural Cells in Vivo." Science, Aug. 2002, 297(5585): 1299.

Chamberlain, G. et al., "Concise Review: Mesenchymal Stem Cells: Their Phenotype, Differentiation Capacity, Immunological Features, and Potential for Homing." Stem Cells, 2007, 25: 2739-2749.

Charoonpatrapong, K. et al., "HMGB1 Expression and Release by Bone Cells." Journal of Cellular Physiology, 2006, 207(2): 480-490.

Chen, X. et al., "Human Bone Marrow Stromal Cell Cultures Conditioned by Traumatic Brain Tissue Extracts: Growth Factor Production." Journal of Neuroscience Research, 2002, 69: 687-691.

Chen, Y. et al., "Coaxing bone marrow stromal mesenchymal stem cells towards neuronal differentiation: progress and uncertainties." Cellular and Molecular Life Sciences, 2006, 63(14): 1649-1657.

Chen, T., et al., "Involvement of high mobility group box-1 in imiquimod-induced psoriasis-like mice model." Journal of Dermatology, 2017, 44: 573-581.

Chopp, M., Li, Y., "Treatment of neural injury with marrow stromal cells." The Lancet Neurology, Jun. 2002, 1(2): 92-100.

Chou, D.K.H. et al., "Identity of nuclear high-mobility-group protein, HMG-1, and sulfoglucuronyl carbohydrate-binding protein, SBP-1, in brain." Journal of Neurochemistry, 2001, 77(1): 120-131.

Cole, J.S.III, "Pharmacologic Mobilization of Mesenchymal Stem Cells for Enhanced Bone Formation" Colby College, Rush University, 2009, Thesis, UMI No. 1466383, 1-82.

Degryse, B. et al., "The High Mobility Group (HMG) Boxes of the Nuclear Protein HMG1 Induce Chemotaxis and Cytoskeleton Reorganization in Rat Smooth Muscle Cells." The Journal of Cell Biology, Mar. 2001, 152(6): 1197-1206.

Delarosa, O., Lombardo, E., "Modulation of Adult Mesenchymal Stem Cells Activity by Toll-Like Receptors: Implications on Therapeutic Potential." Mediators of Inflammation, 2010 vol. 2010, Article ID: 865601, pp. 1-9.

Desai, N. P., Hubbell, J. A., "Tissue response to intraperitoneal implants of polyethylene oxide-modified polyethylene terephthalate." Biomaterials, 1992, 13(8): 505-510.

Desantis, S. et al., "TNFα Deficiency Results in Increased IL-1β in an Early Onset of Spontaneous Murine Colitis." Cell Death and Disease, 2017, 8: e2993, pp. 1-7.

De Souza, A.W.S. et al., "HMGB1 in vascular diseases: its role in vascular inflammation and atherosclerosis." Autoimmunity Reviews, 2012, 11: 909-917.

Dong, Y. et al., "HMGB1 Protein Does Not Mediate the Inflammatory Response in Spontaneous Spinal Cord Regeneration." The Journal of Biological Chemistry, Jun. 11, 2013, 288(25): 18204-18218.

Eckert, R.L. et al., "S100 Proteins in the Epidermis." The Journal of Investigative Dermatology, 2004, 123(1): 23-33.

Ehrchen, J.M. et al., "The endogenous Toll-like receptor 4 agonist S100A8/S100A9 (calprotectin) as innate amplifier of infection, autoimmunity, and cancer." Journal of Leukocyte Biology, Sep. 2009, 86: 557-566.

Erlandsson, H. et al., "The nuclear protein HMGB1 as a proinflammatory mediator," European Journal of Immunology, 2004, 34(6): 1503-1512.

Esposito, E. et al., "Melatonin reduces stress-activated/mitogen-activated protein kinases in spinal cord injury." J. Pineal. Res., 2009, 46: 79-86.

Fang, P. et al., "HMGB1 Contributes to Regeneration After Spinal Cord Injury in Adult Zebrafish." Mol. Neurobio., 2014, 49: 472-483.

Forte, G. et al., "Hepatocyte Growth Factor Effects on Mesenchymal Stem Cells: Proliferation, Migration, and Differentiation." Stem Cells, 2006, 24: 23-33.

Frankel, A.E., et al., "Characterization of Diphtheria Fusion Proteins Targeted to the Human Interleukin-3 Receptor." Protein Engineering, 2000, 13(8): 575-581.

Fritsch, A., et al., "A Hypomorphic Mouse Model of Dystrophic Epidermolysis Bullosa Reveals Mechanisms of Disease and Response to Fibroblast Therapy." The Journal of Clinical Investigation, May 2008, 118(5): 1669-1679.

Fujii, M. et al., "Roles of Bone Morphogenetic Protein Type I Receptors and Smad Proteins in Osteoblast and Chondroblast Differentiation." Molecular Biology of the Cell, Nov. 1999, 10(11): 3801-3813.

Fukushima, N., et al., "Registry Report on Heart Transplantation in Japan (Jun. 2016)." Circulation Journal, 2017, 81: 298-303.

Gallina, C., et al., "A New Paradigm in Cardiac Regeneration: The Mesenchymal Stem Cell Secretome." Stem Cells International, 2015, vol. 2015, Article ID 765846, pp. 1-10.

Germani, A. et al., "Pivotal Advance: High-mobility group box 1 protein-a cytokine with a role in cardiac repair," Journal of Leukocyte Biology, Jan. 2007, 81(1): 41-45.

Gong, W. et al., "The Anti-Inflammatory Activity of HMGB1 A Box is Enhanced When Fused with C-Terminal Acidic Tail," Journal of Biomedicine and Biotechnology, 2010, vol. 2010, Article ID 915234, pp. 1-6.

(56) References Cited

OTHER PUBLICATIONS

Goto, et al., "Investigation of the application of myocardial regeneration inducing therapy using HMGB1 to cardiac infarction." Regenerative Medicine, Feb. 1, 2017, 16: 289.

Granero-Molto, F. et al., "Role of mesenchymal stem cells in regenerative medicine: application to bone and cartilage repair," Expert Opinion on Biological Therapy, 2008, 8(3): 255-268.

Gudjonsson, J. et al., "Chapter 18—Psoriasis." Fitzpatrick's Dermatology in General Medicine, 8th edition, New York: Mc-Graw Hill Medical, 2012, pp. 197-217.

Gueukdjian S.A., "Intra-Arterial Injections in the Treatment of Peripheral Vascular Disease," Postgrad Medical Journal, Jan. 1955, 31(351): 30-31.

\* cited by examiner

SEQUENCE LISTING

```
<160> NUMBER OF SEQ ID NOS: 3

<210> SEQ ID NO 1
<211> LENGTH: 44
<212> TYPE: PRT
<213> ORGANISM: Artificial sequence
<220> FEATURE:
<223> OTHER INFORMATION: An artificially synthesized peptide sequence

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys
            35                  40

<210> SEQ ID NO 2
<211> LENGTH: 215
<212> TYPE: PRT
<213> ORGANISM: Homo sapiens

<400> SEQUENCE: 2

Met Gly Lys Gly Asp Pro Lys Lys Pro Arg Gly Lys Met Ser Ser Tyr
1               5                   10                  15
```

```
Ala Phe Phe Val Gln Thr Cys Arg Glu Glu His Lys Lys His Pro
             20                  25                  30

Asp Ala Ser Val Asn Phe Ser Glu Phe Ser Lys Lys Cys Ser Glu Arg
             35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
                180                 185                 190

Asp Glu Glu Asp Glu Glu Glu Glu Asp Glu Glu Asp Glu Asp Glu
                195                 200                 205

Glu Glu Asp Asp Asp Asp Glu
    210                 215

<210> SEQ ID NO 3
<211> LENGTH: 648
<212> TYPE: DNA
<213> ORGANISM: Homo sapiens

<400> SEQUENCE: 3
atgggcaaag gagatcctaa gaagccgaga ggcaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaaagcgga caaggcccgt tatgaaagag aaatgaaaac ctatatccct     240
cccaaagggg agacaaaaaa gaagttcaag gatcccaatg cacccaagag gcctccttcg     300
gccttcttcc tcttctgctc tgagtatcgc ccaaaaatca aaggagaaca tcctggcctg     360
tccattggtg atgttgcgaa gaaactggga gagatgtgga ataacactgc tgcagatgac     420
aagcagcctt atgaaaagaa ggctgcgaag ctgaaggaaa aatacgaaaa ggatattgct     480
gcatatcgag ctaaaggaaa gcctgatgca gcaaaaaagg gagttgtcaa ggctgaaaaa     540
agcaagaaaa agaaggaaga ggaggaagat gaggaagatg aagaggatga ggaggaggag     600
gaagatgaag aagatgaaga tgaagaagaa gatgatgatg atgaataa                  648
```

THERAPEUTIC AGENT FOR INFLAMMATORY BOWEL DISEASE

CROSS REFERENCE TO A RELATED APPLICATION

This application is a National Stage Application of International Application Number PCT/JP2018/044122, filed Nov. 30, 2018; which claims priority to U.S. Provisional Application No. 62/593,310, filed Dec. 1, 2017 and Japanese Application No. 2018-020686, filed Feb. 8, 2018.

The Sequence Listing for this application is labeled "G6-A1801Psq.txt", which was created on Nov. 26, 2018, and is 4 KB. The entire content is incorporated herein by reference in its entirety.

TECHNICAL FIELD

The present application relates to pharmaceutical compositions for the prevention and/or treatment of inflammatory bowel diseases, which comprise a fragment peptide of the high mobility group box 1 (HMGB1) protein.

BACKGROUND ART

Inflammatory bowel diseases (IBDs) are intractable diseases where chronic inflammation and/or ulcers develop in the mucosa of the intestinal tract. Typical examples of the diseases include ulcerative colitis and Crohn's disease. Although the cause of inflammatory bowel diseases is not yet fully elucidated, it is believed that the intricate involvement of genetic factors and various environmental factors causes abnormalities in the immune system, which result in the diseases. However, inflammatory bowel diseases have no radical treatment at present and frequently repeat remissions and relapses. Accordingly, long-term medical management is required.

As therapeutic agents for inflammatory bowel diseases, 5-aminosalicylic acid preparations, corticosteroid preparations, immunosuppressants, biological preparations (e.g., anti-TNF-$\alpha$ antibodies and anti-$\alpha 4\beta 7$ integrin antibodies), and such are used; however, there are cases where sufficient effect cannot be obtained. Furthermore, in terms of side effects, there is room for improvement since the following problems and such exist: nausea, fever, abdominal pain, anemia, interstitial nephritis, and hepatic dysfunction caused by 5-aminosalicylic acid preparations; insomnia, osteoporosis, adrenocortical dysfunction, impaired glucose tolerance, and increased blood pressure caused by corticosteroid preparations; and renal dysfunction, hepatic dysfunction, leukopenia, and increased blood pressure caused by immunosuppressants. Therefore, development of a safer and more effective therapeutic agent for inflammatory bowel diseases, the type of which is different from existing therapeutic agents, is desired.

CITATION LIST

Patent Literature

[PTL 1] WO2012/147470
[PTL 2] WO2014/065347
[PTL 3] WO2014/065348

SUMMARY OF INVENTION

Technical Problem

An objective of the present application is to provide novel pharmaceuticals that are effective in the treatment of inflammatory bowel diseases.

Solution to Problem

As a result of searching for substances that are effective in the treatment of inflammatory bowel diseases, the present inventors discovered that an HMGB1 fragment peptide having a specific amino acid sequence exhibits an effect of suppressing weight loss and an effect of suppressing shortening of the large intestine and mucosal damage in an animal model of inflammatory bowel diseases. Accordingly, the present application provides pharmaceutical compositions for the prevention and/or treatment of inflammatory bowel diseases, which comprise the specific HMGB1 fragment peptide.

Namely, the present application provides the following:
[1]
A pharmaceutical composition for the prevention and/or treatment of an inflammatory bowel disease, comprising a substance described in any of following (a) to (c) (herein below referred to as substance A):
 (a) an HMGB1 fragment peptide comprising the amino acid sequence described in SEQ ID NO: 1;
 (b) a peptide comprising an amino acid sequence in which one or more amino acids are substituted, deleted, inserted, or added in the amino acid sequence described in SEQ ID NO: 1; and
 (c) a peptide comprising an amino acid sequence having about 80% or more sequence identity with the amino acid sequence described in SEQ ID NO: 1.
[2]
The pharmaceutical composition of [1], wherein the inflammatory bowel disease is a non-specific inflammatory bowel disease.
[3]
The pharmaceutical composition of [2], wherein the non-specific inflammatory bowel disease is ulcerative colitis.
[4]
The pharmaceutical composition of [2], wherein the non-specific inflammatory bowel disease is Crohn's disease.
[5]
A pharmaceutical composition for suppressing weight loss or intestinal mucosal damage in a patient with an inflammatory bowel disease, comprising substance A.
[6]
The pharmaceutical composition of [5], wherein the inflammatory bowel disease is a non-specific inflammatory bowel disease.
[A1]
A method of preventing and/or treating an inflammatory bowel disease, comprising administering an effective amount of substance A to a subject.
[A2]
The method of [A1], wherein the inflammatory bowel disease is a non-specific inflammatory bowel disease.
[A3]
The method of [A2], wherein the non-specific inflammatory bowel disease is ulcerative colitis.
[A4]
The method of [A2], wherein the non-specific inflammatory bowel disease is Crohn's disease.

[A5]

A method of suppressing weight loss or intestinal mucosal damage in a patient with inflammatory bowel disease, comprising administering an effective amount of substance A to the patient.

[A6]

The method of [A5], wherein the inflammatory bowel disease is a non-specific inflammatory bowel disease.

[B1]

Substance A for use in the prevention and/or treatment of an inflammatory bowel disease.

[B2]

The substance A of [B1], wherein the inflammatory bowel disease is a non-specific inflammatory bowel disease.

[B3]

The substance A of [B2], wherein the non-specific inflammatory bowel disease is ulcerative colitis.

[B4]

The substance A of [B2], wherein the non-specific inflammatory bowel disease is Crohn's disease.

[B5]

Substance A for use in the suppression of weight loss or intestinal mucosal damage in an inflammatory bowel disease patient.

[B6]

The substance A of [B5], wherein the inflammatory bowel disease is a non-specific inflammatory bowel disease.

[C1]

Use of substance A in the manufacture of a medicament for the prevention and/or treatment of an inflammatory bowel disease.

[C2]

The use of [C1], wherein the inflammatory bowel disease is a non-specific inflammatory bowel disease.

[C3]

The use of [C2], wherein the non-specific inflammatory bowel disease is ulcerative colitis.

[C4]

The use of [C2], wherein the non-specific inflammatory bowel disease is Crohn's disease.

[C5]

Use of substance A in the manufacture of a medicament for the suppression of weight loss or intestinal mucosal damage in a patient with inflammatory bowel disease.

[C6]

The use of [C5], wherein the inflammatory bowel disease is a non-specific inflammatory bowel disease.

DESCRIPTION OF EMBODIMENTS

Figure 1:
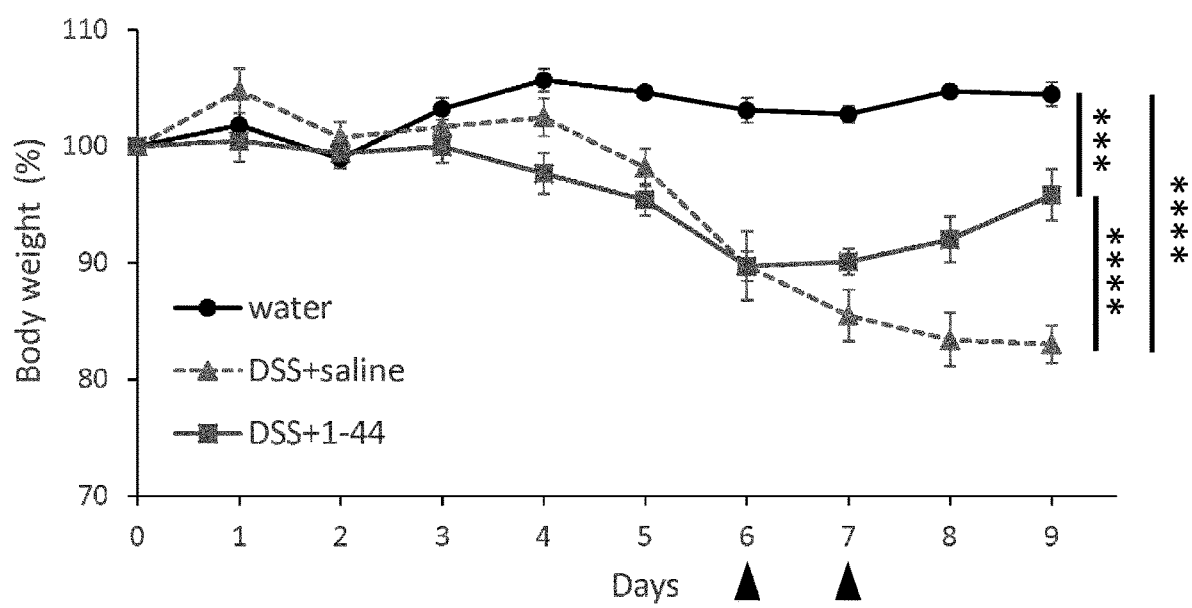
FIG. 1 is a graph showing the body weight change of the mice (* $p<0.001$, ** $p<0.0001$). In the graph, "Water" indicates the normal mice, "DSS+saline" indicates the control group, and "DSS+1-44" indicates the HMGB1 peptide (1-44) administration group, respectively. On the horizontal axis, the number of days shows the days after the start of drinking of the dextran sulfate sodium (DSS) aqueous solution and the triangular marks show the days of administration in the control group and the HMGB1 peptide (1-44) administration group.

The present application provides pharmaceutical compositions for the prevention and/or treatment of inflammatory bowel diseases, which comprise an HMGB1 fragment peptide comprising the amino acid sequence described in SEQ ID NO: 1.

In the present application, inflammatory bowel diseases (hereinafter, also referred to as IBDs) include diseases of unknown cause (non-specific inflammatory bowel diseases) and diseases having a clear relationship with cause (specific inflammatory bowel diseases). Non-specific inflammatory bowel diseases include, but are not limited to, ulcerative colitis, Crohn's disease, and intestinal Behcet disease. Specific inflammatory bowel diseases include, but are not limited to, infectious enteritis, drug-induced enteritis, ischemic enteritis, and intestinal tuberculosis. In one embodiment, the inflammatory bowel diseases of the present application are non-specific inflammatory bowel diseases. In a further embodiment, the non-specific inflammatory bowel diseases of the present application are ulcerative colitis or Crohn's disease. In another embodiment, the non-specific inflammatory bowel diseases of the present application are ulcerative colitis. In further another embodiment, the non-specific inflammatory bowel diseases of the present application are Crohn's disease.

Ulcerative colitis is an inflammatory disease of unknown cause where erosion and ulcers occur in the mucosa of the large intestine. Symptoms such as bloody stool, mucous and bloody stool, diarrhea or bloody diarrhea, and abdominal pain are presented as main symptoms and are often accompanied by fever and weight loss.

Crohn's disease is a chronic inflammatory disease of unknown cause where granulomatous inflammatory lesions with ulcers and fibrosis develop in the gastrointestinal tract. In addition to the presentation of main symptoms such as abdominal pain, diarrhea, weight loss, and fever, intestinal complications such as fistulas and stenosis and extraintestinal complications such as anemia, arthritis, iritis, erythema nodosum, and anal lesions may occur.

In the present application, the term "pharmaceutical composition" is used interchangeably with "medicament", "drug", or "pharmacological composition".

The present application also provides pharmaceutical compositions for suppressing weight loss or intestinal mucosal damage in patients with an inflammatory bowel disease, which comprise an HMGB1 fragment peptide comprising the amino acid sequence described in SEQ ID NO: 1. In one embodiment, the pharmaceutical compositions of the present application are used for suppressing mucosal damage in the large intestine of patients with an inflammatory bowel disease.

In the present application, an HMGB1 fragment peptide comprising the amino acid sequence described in SEQ ID NO: 1 refers to a peptide consisting of a portion of the HMGB1 protein and comprising the amino acid sequence described in SEQ ID NO: 1. Such a peptide can be obtained as genetic recombinants by incorporating DNA encoding the peptide into an appropriate expression system or can be synthesized artificially.

In the present application, examples of the HMGB1 protein include, but are not limited to, proteins comprising the amino acid sequence described in SEQ ID NO: 2 and proteins encoded by DNA comprising the nucleotide sequence described in SEQ ID NO: 3.

Examples of the HMGB1 fragment peptide comprising the amino acid sequence described in SEQ ID NO: 1 in the present application include, but are not limited to, an HMGB1 fragment peptide consisting of the amino acid sequence described in SEQ ID NO: 1.

In the pharmaceutical compositions of the present application, peptides that comprise an amino acid sequence with one or more amino acid residues modified (substituted, deleted, inserted, or added) in the amino acid sequence described in SEQ ID NO: 1 and that are functionally equivalent to an HMGB1 fragment peptide comprising the amino acid sequence described in SEQ ID NO: 1 can be used instead of or in combination with an HMGB1 fragment peptide comprising the amino acid sequence described in SEQ ID NO: 1. Examples of such peptides include, but are not limited to, the following:

i) a peptide comprising an amino acid sequence in which one or more amino acids (e.g., one to ten, one to nine, one to eight, one to seven, one to six, one to five, one to four, one to three, or one or two) have been substituted, deleted, inserted, or added in the amino acid sequence described in SEQ ID NO: 1;

ii) a peptide consisting of an amino acid sequence in which one or more amino acids (e.g., one to ten, one to nine, one to eight, one to seven, one to six, one to five, one to four, one to three, or one or two) have been substituted, deleted, inserted, or added in the amino acid sequence described in SEQ ID NO: 1;

iii) a peptide comprising an amino acid sequence having about 80% or more, for example, about 85% or more, about 90% or more, about 91% or more, about 92% or more, about 93% or more, about 94% or more, about 95% or more, about 96% or more, about 97% or more, about 98% or more, or about 99% or more sequence identity with the amino acid sequence described in SEQ ID NO: 1; and iv) a peptide consisting of an amino acid sequence having about 80% or more, for example, about 85% or more, about 90% or more, about 91% or more, about 92% or more, about 93% or more, about 94% or more, about 95% or more, about 96% or more, about 97% or more, about 98% or more, or about 99% or more sequence identity with the amino acid sequence described in SEQ ID NO: 1.

An effective amount of the peptide of the present application or a pharmaceutical composition comprising the peptide (hereinafter, referred to as the peptide or such) is administered to a subject for the treatment or prevention of the diseases or symptoms described herein.

An effective amount as used herein refers to an amount sufficient for the treatment or prevention of the diseases or symptoms as described herein. Treatment in the present application includes, but is not limited to, alleviation, delay, blockade, improvement, remission, cure, and complete cure. Prevention in the present application includes, but is not limited to, alleviation, delay, and blockade.

Subjects in the present application include, without limitation, mammals, birds, fish, and such. Mammals include, but are not limited to, humans and non-human animals, for example, humans, mice, rats, monkeys, pigs, dogs, rabbits, hamsters, guinea pigs, horses, sheep, and whales. In the present application, the term "subject" is used interchangeably with "patient", "individual", and "animal".

There is no limitation on the site of administration of the peptide or such of the present application, and the peptide or such of the present application can exert its effect when administered to any site, such as a site where a symptom of inflammatory bowel diseases appears or a site nearby, a site different from these sites (a site other than these sites), a site separated from a site where a symptom of inflammatory bowel diseases appears, a site distal from a site where a symptom of inflammatory bowel diseases appears, or a site distal and ectopic to a site where a symptom of inflammatory bowel diseases appears.

The peptide or such of the present application can also exert its effect when administered to any tissue, such as a tissue different from a tissue where a symptom of inflammatory bowel diseases appears (e.g., the gastrointestinal tract), a tissue separated from a tissue where a symptom of inflammatory bowel diseases appears, a tissue distal from a tissue where a symptom of inflammatory bowel diseases appears, or a tissue distal and ectopic to a tissue where a symptom of inflammatory bowel diseases appears.

Methods of administering the peptide or such of the present application include, but are not limited to, oral administration and parenteral administration. Methods of parenteral administration include, but are not limited to, intravascular (intra-arterial, intravenous, and such), intramuscular, subcutaneous, intradermal, intraperitoneal, nasal, pulmonary, and transdermal administrations. The peptide or such of the present application can also be administered systemically or locally (e.g., subcutaneously, intradermally, or to the skin surface, eyeball or palpebral conjunctiva, nasal mucosa, oral and gastrointestinal mucosa, vaginal and endometrial mucosa, or injured site) by injection administration, for example, intravenous injection, intramuscular injection, intraperitoneal injection, and subcutaneous injection.

Furthermore, in place of the peptide or such of the present application, cells secreting the peptide of the present application, gene therapy vectors into which DNA encoding the peptide has been inserted, and pharmaceutical compositions containing them can be used.

Moreover, the administration method can be appropriately selected according to the age and symptoms of a patient. When administering the peptide of the present application, the dose can be selected, for example, from the range of 0.0000001 mg to 1000 mg per kilogram of body weight per administration. Alternatively, the dose can be selected, for example, from the range of 0.00001 to 100000 mg/body for a patient. When administering cells secreting the peptide of the present application or gene therapy vectors into which DNA encoding the peptide has been inserted, they can be administered so that the amount of the peptide is within the above range. However, the pharmaceutical compositions in the present application are not limited to these dosages.

The pharmaceutical compositions of the present application can be formulated according to conventional methods (e.g., Remington's Pharmaceutical Science, latest edition, Mark Publishing Company, Easton, U.S.A.), and may contain pharmaceutically acceptable carriers and additives together. Examples include, but are not limited to, surfactants, excipients, coloring agents, perfumes, preservatives, stabilizers, buffers, suspending agents, isotonizing agents, binding agents, disintegrants, lubricants, fluidity-promoting agents, and flavoring agents. Other commonly used carriers can also be used as appropriate. Specific examples include, light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain fatty acid triglycerides, polyoxyethylene hydrogenated castor oil 60, white sugar, carboxymethyl cellulose, cornstarch, and inorganic salts.

All prior art documents cited herein are incorporated herein as references.

The present invention is further illustrated by, but not limited to, the examples below.

EXAMPLE

Example 1

Figure 2:
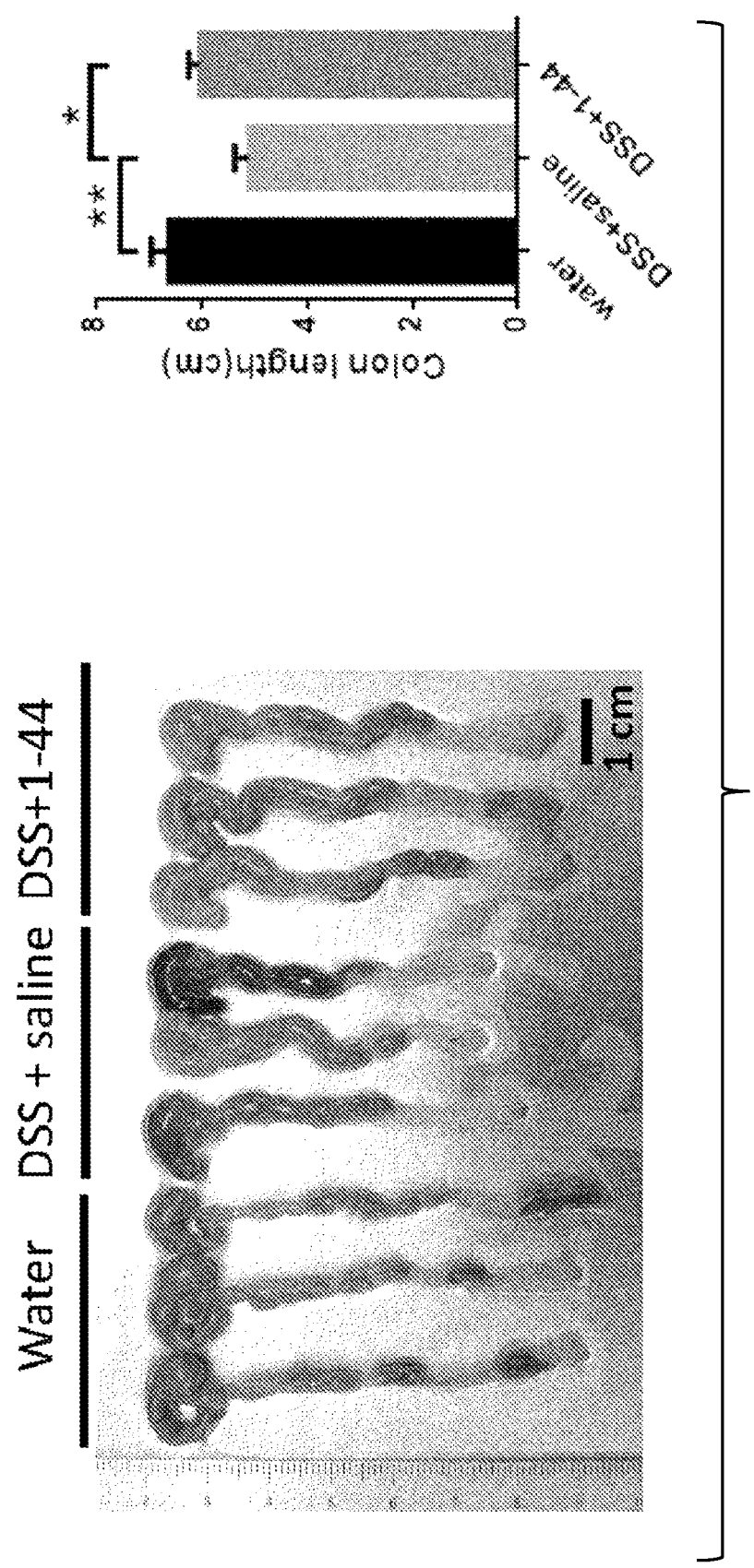
FIG. 2 presents a photograph of the large intestines excised from the mice on the 9th day after the start of drinking of the DSS aqueous solution and a graph showing the length of the large intestines (* $p<0.05$, ** $p<0.01$).
Figure 3:
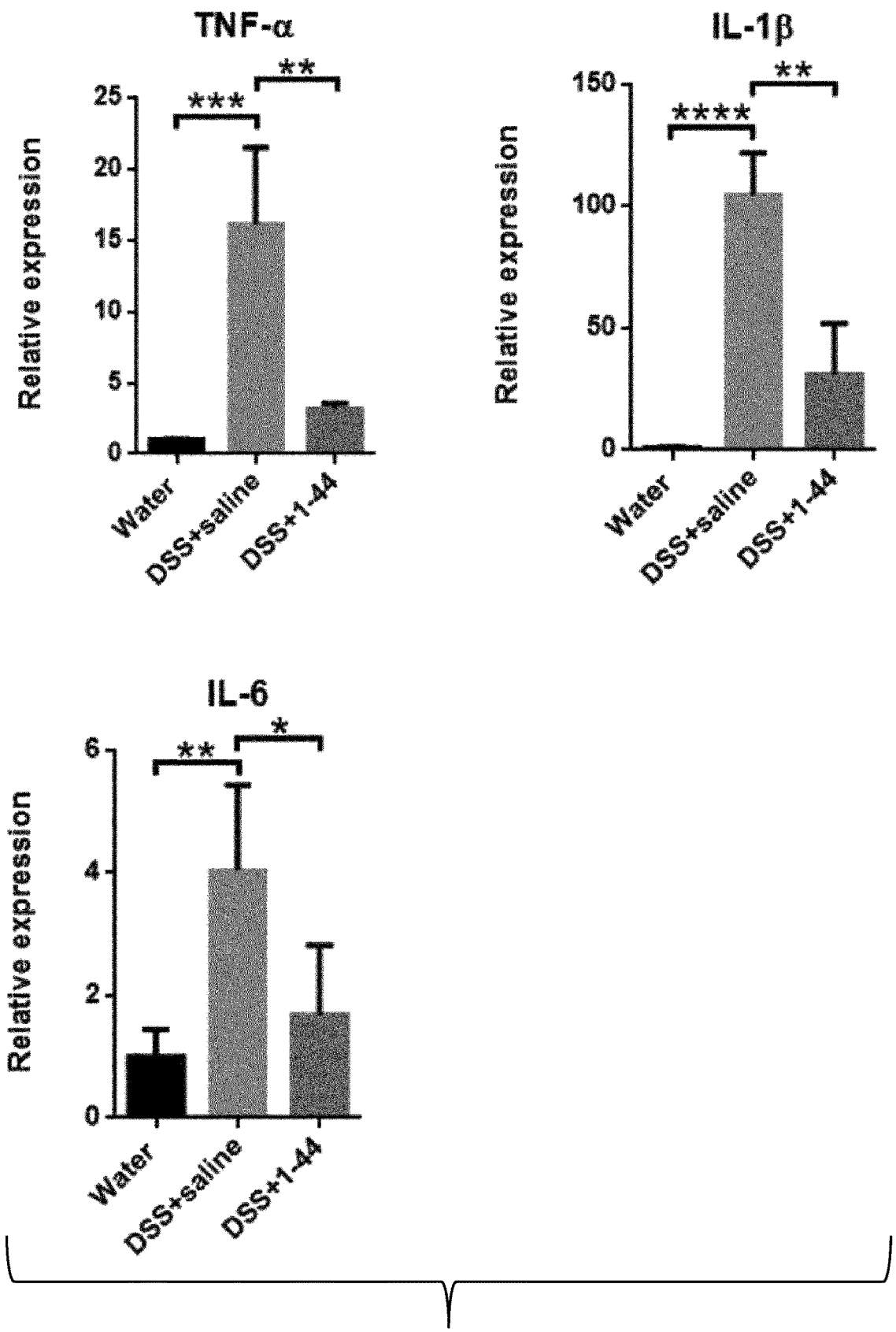
FIG. 3 presents graphs showing the expression levels of inflammatory cytokines in the large intestine on the 9th day after the start of drinking of the DSS aqueous solution (* $p<0.05$,  $p<0.01$, * $p<0.001$, **** $p<0.0001$).

Efficacy Evaluation of an HMGB1 Fragment Peptide for Inflammatory Bowel Diseases (1)
(1) Materials and Methods
i) Drug Preparation Dextran sulfate sodium (DSS) (molecular weight 5,000 to 6,000, manufactured by Nacalai Tesque, catalog No. 10930-94) was dissolved in water to prepare a 3% (w/v) DSS aqueous solution. A peptide consisting of amino acid residues 1-44 of the human-derived HMGB1 protein (SEQ ID NO: 1) was chemically synthesized by a solid-phase method. Hereinafter, the HMGB1 fragment peptide is referred to as the HMGB1 peptide (1-44) and is expressed as an abbreviation "1-44" in the drawings corresponding to the Examples.
ii) Production of Inflammatory Bowel Disease (IBD) Model Mice Colitis was induced in C57BL/6 mice (8 to 10-week-old, male, body weight about 20 g) by allowing them to freely drink the 3% DSS aqueous solution in place of purified water (RO water) (drinking of the DSS aqueous solution was continued until the removal of the large intestine). Mice that were allowed to freely drink purified water (RO water) (hereinafter, referred to as "normal mice") were used as comparative subjects.
iii) Peptide Administration The IBD model mice produced as described above were divided into the HMGB1 peptide (1-44) administration group (n=3) and the control group (n=3). The test substance was administered by injecting an HMGB1 peptide (1-44) solution, which has been adjusted to a concentration of 0.5 mg/ml with saline as the vehicle, into the vein at a dose of 200 µl/animal (5 mg/kg as the peptide dose) on the 6th and 7th days after the start of drinking the DSS aqueous solution. In the control group, saline was injected into the vein at a dose of 200 µl/animal on the 6th and 7th days after the start of drinking the DSS aqueous solution. No substance was administered to the normal mice (n=3). Hereinafter, "the Xth day after the start of drinking the DSS aqueous solution" is expressed as an abbreviation "the Xth day of DSS drinking".
iv) Evaluation of the Effect of Peptide Administration The body weight of the mice was measured daily from the start of drinking the DSS aqueous solution until the removal of the large intestine. On the 9th day of DSS drinking, the large intestine was excised from the mice, and the length of the large intestine was measured. mRNA was extracted from the terminal part near the anus in the excised large intestine, and the expression level of inflammatory cytokines (TNF-α, IL-1β, and IL-6) was analyzed by quantitative PCR.
(2) Results
i) Body Weight Change FIG. 1 shows the change in body weight of the mice during the test period (see "Water" for the normal mice, "DSS+saline" for the control group, and "DSS+1-44" for the HMGB1 peptide (1-44) administration group). The body weight of the IBD model mice in the control group decreased as the days passed and became significantly lower than that of the normal mice on the 9th day of DSS drinking. By contrast, in the HMGB1 peptide (1-44) administration group, the once decreased body weight recovered after the peptide administrations and became significantly higher than that of the control group on the 9th day of DSS drinking.
ii) Large Intestine Length As shown in FIG. 2, under the conditions where the large intestine length of the IBD model mice in the control group was significantly shorter than that of the normal mice, the length of the large intestine in the HMGB1 peptide (1-44) administration group was significantly longer than that of the control group (see "Water" for the normal mice, "DSS+saline" for the control group, and "DSS+1-44" for the HMGB1 peptide (1-44) administration group). These results indicate that the administration of the HMGB1 peptide (1-44) suppressed shortening of the large intestine in DSS-induced enteritis, which is a model of IBDs.
iii) Inflammatory Cytokines FIG. 3 shows the expression levels of inflammatory cytokines in the large intestine on the 9th day of DSS drinking (see "Water" for the normal mice, "DSS+saline" for the control group, and "DSS+1-44" for the HMGB1 peptide (1-44) administration group). In the IBD model mice of the control group, the expression level of TNF-α, IL-1β, and IL-6 was significantly higher than that of the normal mice. Meanwhile, the expression level of TNF-α, IL-1β, and IL-6 in the HMGB1 peptide (1-44) administration group was significantly lower than that of the control group. These results indicate that the administration of the HMGB1 peptide (1-44) suppressed the expression of inflammatory cytokines in DSS-induced enteritis, which is a model of IBDs.

Example 2

Figure 4:
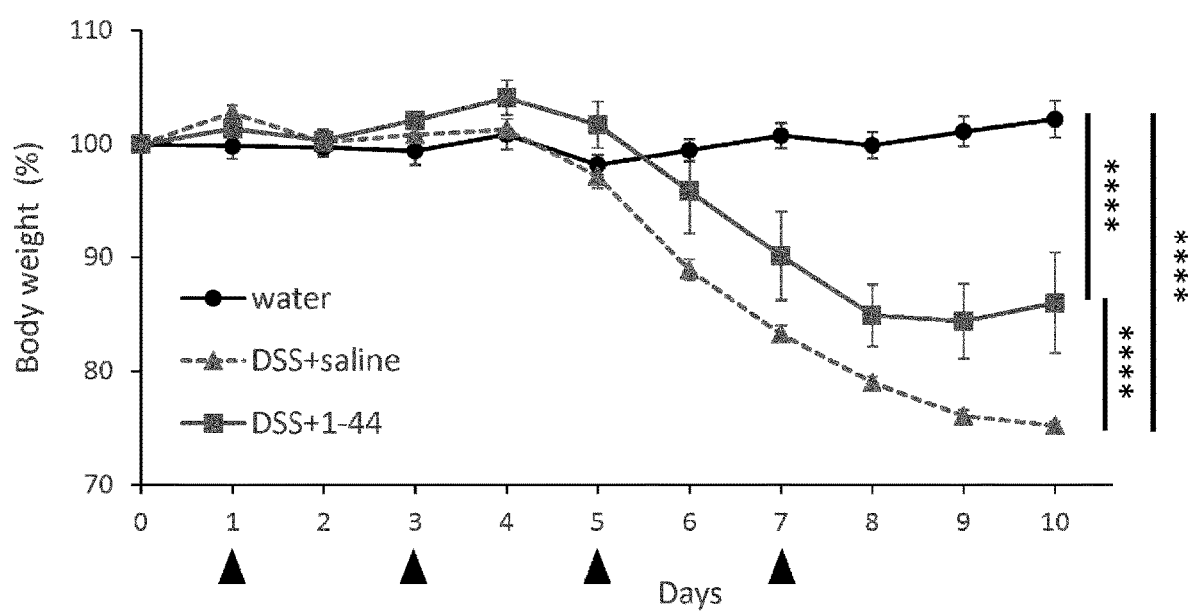
FIG. 4 is a graph showing the body weight change of the mice (**** $p<0.0001$). In the graph, "Water" indicates the normal mice, "DSS+saline" indicates the control group, and "DSS+1-44" indicates the HMGB1 peptide (1-44) administration group, respectively. On the horizontal axis, the number of days shows the days after the start of drinking of the DSS aqueous solution and the triangular marks show the days of administration in the control group and the HMGB1 peptide (1-44) administration group.
Figure 5:
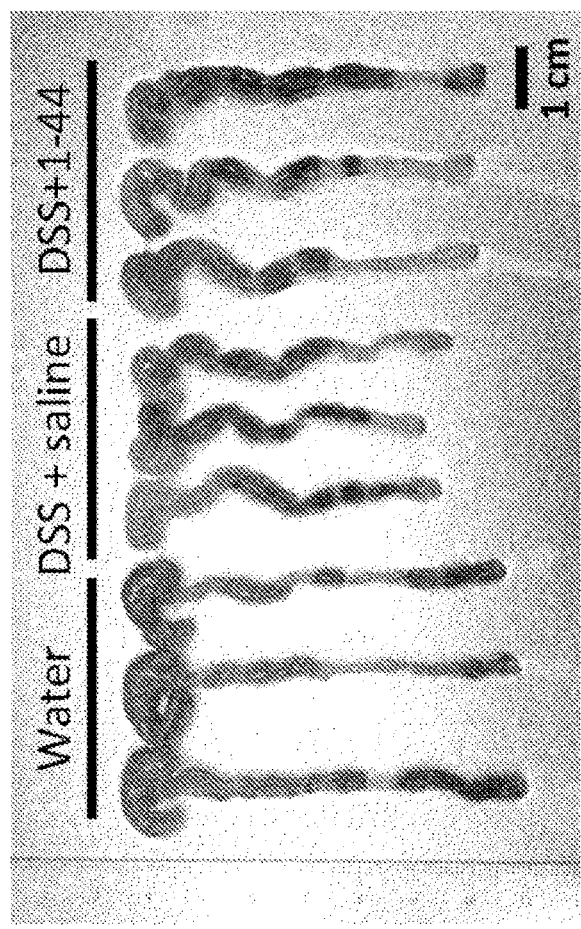
FIG. 5 presents a photograph of the large intestines excised from the mice on the 10th day after the start of drinking of the DSS aqueous solution and a graph showing the length of the large intestines (* $p<0.05$, ** $p<0.01$).
Figure 5:
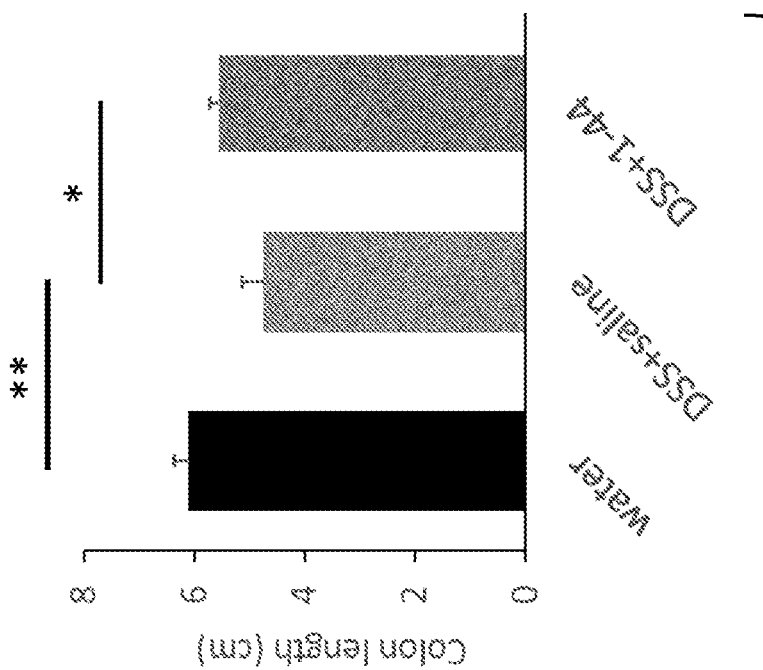
Figure 6:
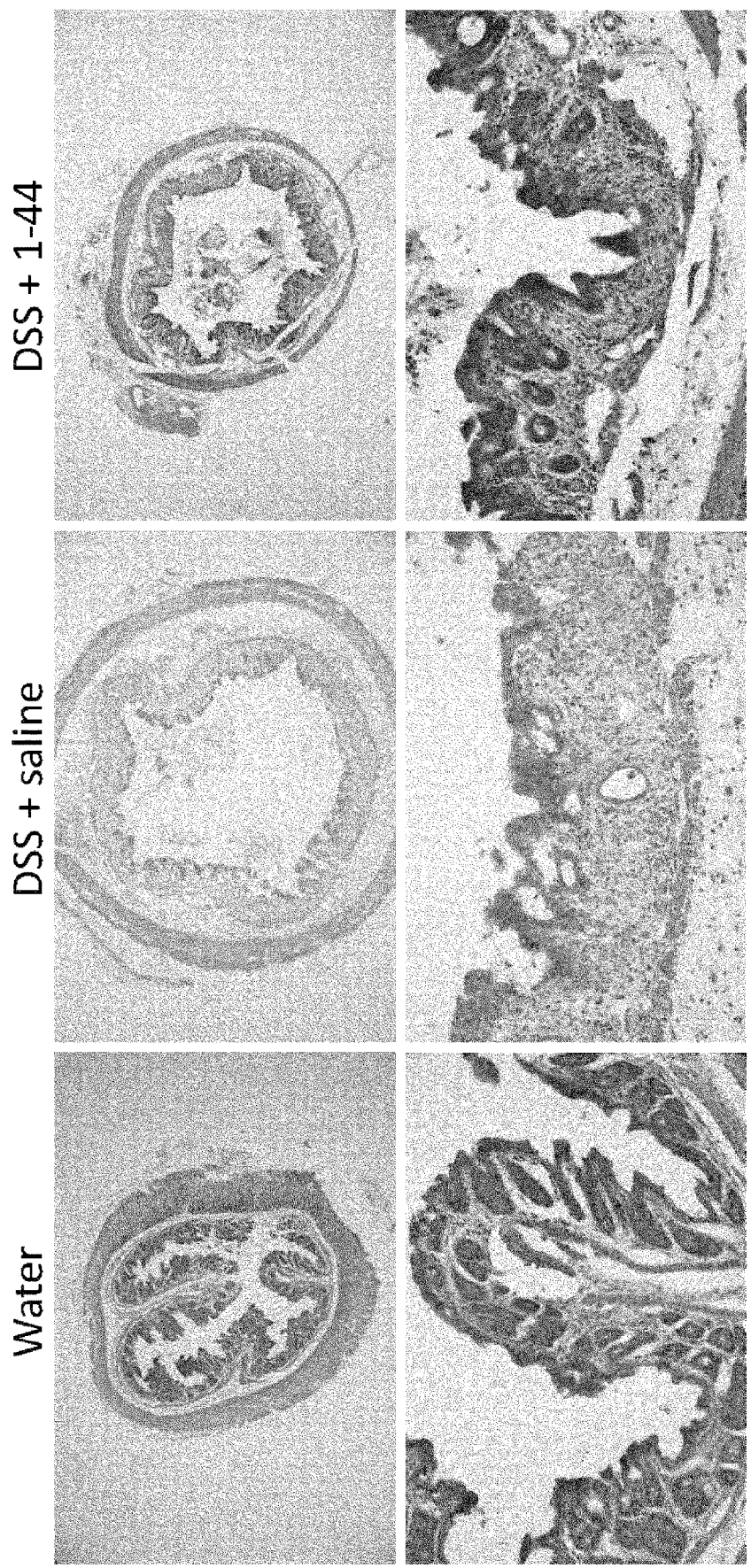
FIG. 6 presents images showing the HE staining results of large intestine tissues on the 10th day after the start of drinking of the DSS aqueous solution.

Efficacy Evaluation of an HMGB1 Fragment Peptide for Inflammatory Bowel Diseases (2)
(1) Materials and Methods
i) Drugs and Mice The DSS aqueous solution and the HMGB1 peptide (1-44) were prepared and the inflammatory bowel disease model mice were produced in the same way as Example 1.
ii) Peptide Administration The IBD model mice produced as described in Example 1 were divided into the HMGB1 peptide (1-44) administration group (n=3) and the control group (n=3). The test substance was administered by injecting an HMGB1 peptide (1-44) solution, which has been adjusted to a concentration of 0.5 mg/ml with saline as the vehicle, into the vein at a dose of 200 µl/animal (5 mg/kg as the peptide dose) on the 1st, 3rd, 5th, and 7th days of DSS drinking. In the control group, saline was injected into the vein at a dose of 200 µl/animal on the 1st, 3rd, 5th, and 7th days of DSS drinking. No substance was administered to the normal mice (n=3).
iii) Evaluation of the Effect of Peptide Administration The body weight of the mice was measured daily from the start of drinking the DSS aqueous solution until the removal of the large intestine. On the 10th day of DSS drinking, the large intestine was excised from the mice, and the length of the large intestine was measured. Tissue sections of the cross-section of the intestinal tract were produced using the terminal part near the anus of the excised large intestine, and hematoxylin-eosin (HE) staining was performed.
(2) Results
i) Body Weight Change FIG. 4 shows the change in body weight of the mice during the test period (see "Water" for the normal mice, "DSS+saline" for the control group, and "DSS+1-44" for the HMGB1 peptide (1-44) administration group). The body weight of the IBD model mice (in the control group and the HMGB1 peptide (1-44) administration group) decreased as the days passed and became significantly lower than that of the normal mice on the 10th day of DSS drinking. In the HMGB1 peptide (1-44) administration group, the decrease in body weight was suppressed compared to the control group, and the body weight on the 10th day of DSS drinking was significantly higher than that of the control group.
ii) Large Intestine Length As shown in FIG. 5, under the conditions where the large intestine length of the IBD model mice in the control group was significantly shorter than that of the normal mice, the length of the large intestine in the HMGB1 peptide (1-44) administration group was significantly longer than that of the control group (see "Water" for the normal mice, "DSS+saline" for the control group, and "DSS+1-44" for the HMGB1 peptide (1-44) administration group). These results indicate that the administration of the HMGB1 peptide (1-44) suppressed shortening of the large intestine in DSS-induced enteritis, which is a model of IBDs.
iii) Mucosal Tissue FIG. 6 shows the HE staining images of large intestine tissues on the 10th day of DSS drinking (see "Water" for the normal mice, "DSS+saline" for the control group, and "DSS+1-44" for the HMGB1 peptide (1-44) administration group). While the mucosal tissue was damaged in the IBD model mice of the control group, damage of the mucosal tissue was suppressed in the HMGB1 peptide (1-44) administration group. These results indicate that the administration of the HMGB1 peptide (1-44) suppressed mucosal tissue damage of the large intestine in DSS-induced enteritis, which is a model of IBDs.

Example 3

Figure 7:
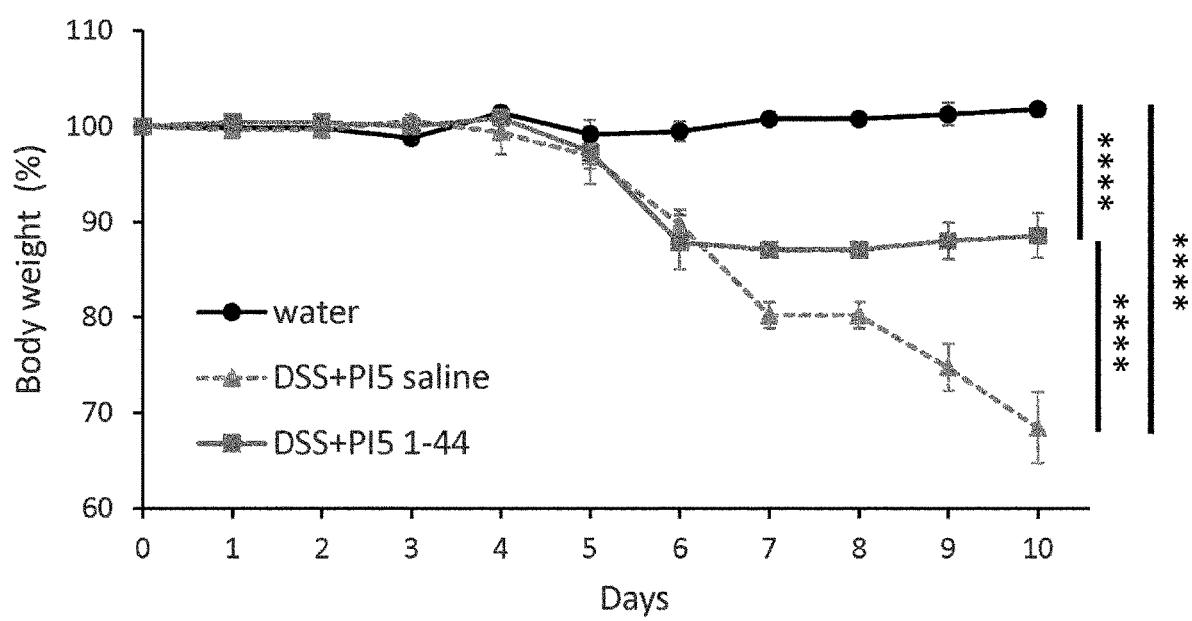
FIG. 7 is a graph showing the body weight change of the mice (**** $p<0.0001$). In the graph, "Water" indicates the normal mice, "DSS+PI5 saline" indicates the control group, and "DSS+PI5 1-44" indicates the HMGB1 peptide (1-44) administration group, respectively. On the horizontal axis, the number of days shows the days after the start of drinking the DSS aqueous solution.
Figure 8:
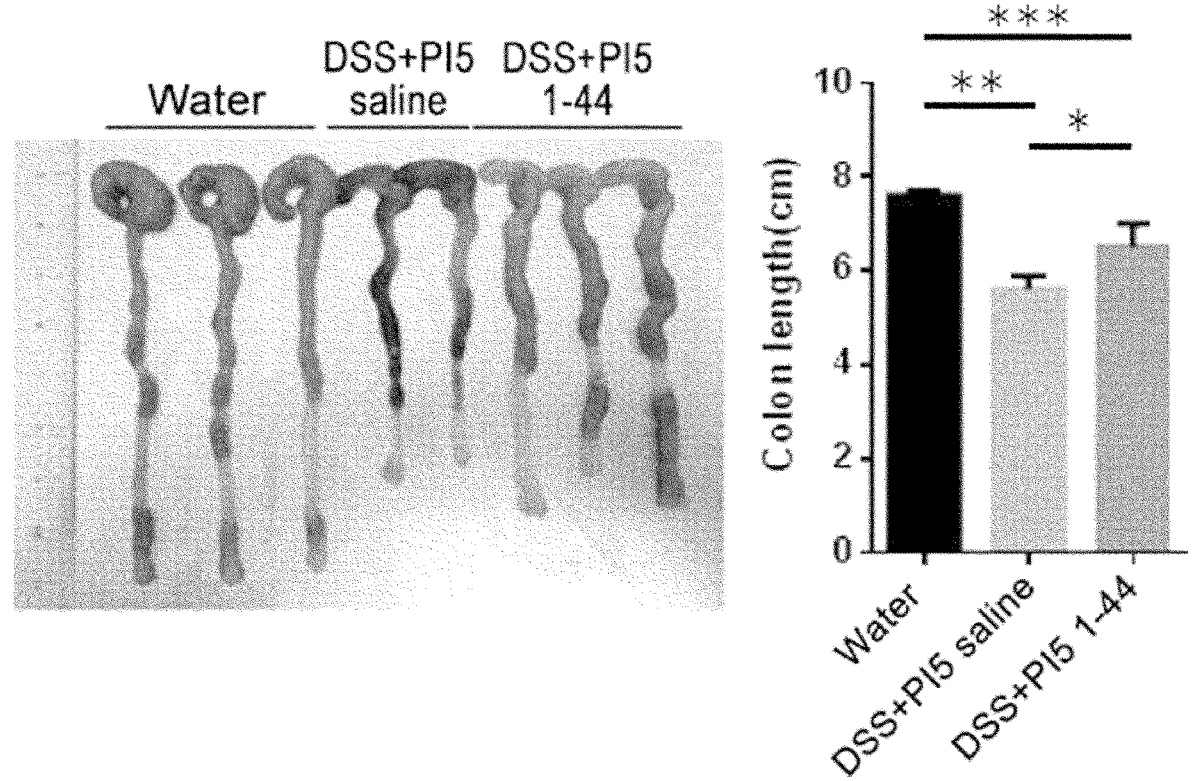
FIG. 8 presents a photograph of the large intestines excised from the mice on the 10th day after the start of drinking of the DSS aqueous solution and a graph showing the length of the large intestines (* $p<0.05$,  $p<0.01$, * $p<0.001$).

Efficacy Evaluation of an HMGB1 Fragment Peptide for Inflammatory Bowel Diseases (3)
(1) Materials and Methods
i) Drugs and Mice The DSS aqueous solution and the HMGB1 peptide (1-44) were prepared and the inflammatory bowel disease model mice were produced in the same way as Example 1.
ii) Preparation of Peptide-Containing Hydrogel A bioabsorbable hydrogel (MedGel (registered trademark) PI5, manufactured by MedGEL CO., LTD) cut into a size of about 5 mm×5 mm was soaked with 20 µl of an HMGB1 peptide (1-44) solution, which has been adjusted to a concentration of 5 µg/µl with saline as the vehicle, by dripping and allowed to stand under ice-cooling for 30 minutes. The resulting hydrogel was used for embedding in the mice of the HMGB1 peptide (1-44) administration group. According to the same procedure as the above, a hydrogel soaked with saline instead of the HMGB1 peptide (1-44) solution was used for embedding in the mice of the control group.
iii) Peptide Administration The IBD model mice produced as described in Example 1 were divided into the HMGB1 peptide (1-44) administration group (n=3) and the control group (n=3). The test substance was administered by embedding the HMGB1 peptide (1-44) solution-containing hydrogel prepared as described above on the back of the mice one day before the start of drinking the DSS aqueous solution. The saline-containing hydrogel prepared as described above was embedded on the back of the mice in the control group one day before the start of drinking the DSS aqueous solution. No substance was administered to the normal mice (n=3).
iv) Evaluation of the Effect of Peptide Administration The body weight of the mice was measured daily from the start of drinking the DSS aqueous solution until the removal of the large intestine. On the 10th day of DSS drinking, the large intestine was excised from the mice, and the length of the large intestine was measured.
(2) Results
i) Body Weight Change FIG. 7 shows the change in body weight of the mice during the test period (see "Water" for the normal mice, "DSS+PI5 saline" for the control group, and "DSS+PI5 1-44" for the HMGB1 peptide (1-44) administration group). The body weight of the IBD model mice (in the control group and the HMGB1 peptide (1-44) administration group) decreased as the days passed and became lower than that of the normal mice on the 10th day of DSS drinking. In the HMGB1 peptide (1-44) administration group, the decrease in body weight was suppressed compared to the control group, and the body weight on the 10th day of DSS drinking was higher than that of the control group.
ii) Large Intestine Length As shown in FIG. 8, under the conditions where the large intestine length of the IBD model mice in the control group was shorter than that of the normal mice, the length of the large intestine in the HMGB1 peptide (1-44) administration group was longer than that of the control group (see "Water" for the normal mice, "DSS+PI5 saline" for the control group, and "DSS+PI5 1-44" for the HMGB1 peptide (1-44) administration group). These results indicate that the administration of the HMGB1 peptide (1-44) suppressed shortening of the large intestine in DSS-induced enteritis, which is a model of IBDs.

Comparative Example 1

Figure 9:
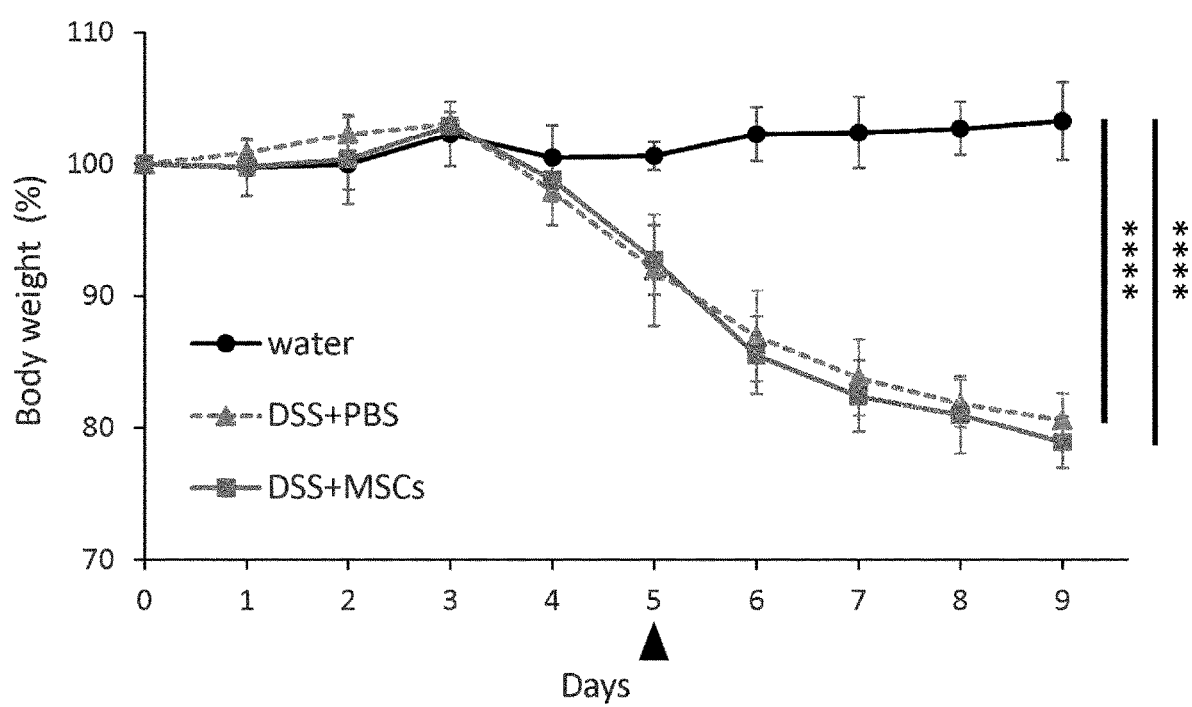
FIG. 9 is a graph showing the body weight change of the mice (**** $p<0.0001$). In the graph, "Water" indicates the normal mice, "DSS+PBS" indicates the control group, and "DSS+MSCs" indicates the MSC administration group, respectively. On the horizontal axis, the number of days shows the days after the start of drinking of the DSS aqueous solution and the triangular mark shows the administration day in the control group and the MSC administration group.

Administration of Mesenchymal Stem Cells (MSCs) to an Inflammatory Bowel Disease Model In recent years, attempts have been made to use mesenchymal stem cells extracted from a living body in the treatment of inflammatory bowel diseases. Meanwhile, the present inventors have so far discovered that the HMGB1 peptide (1-44) has an action of recruiting mesenchymal stem cells in bone marrow into peripheral blood. Therefore, the following experiment was conducted to compare the effects of administering mesenchymal stem cells and administering the HMGB1 peptide (1-44).
(1) Materials and Methods
i) Drugs and Mice The DSS aqueous solution and the HMGB1 peptide (1-44) were prepared and the inflammatory bowel disease model mice were produced in the same way as Example 1.
ii) Administration of Mesenchymal Stem Cells The IBD model mice produced as described in Example 1 were divided into the mesenchymal stem cell (MSC) administration group (n=3) and the control group (n=3). Bone marrow was collected from the femurs of C57BL/6 mice (6 to 8-week-old, male) and cultured on a plastic plate using MesenCult (trademark) MSC Basal Medium (Mouse) (manufactured by STEMCELL Technologies Inc., containing 10 nM Rock inhibitor and MesenPure) as the medium to obtain mesenchymal stem cells as adherent colonies. On the 5th day of DSS drinking, the mesenchymal stem cells after three passages were suspended in PBS and adjusted to $1 \times 10^6$ cells/ml, and 100 µl of the suspension was administered intraperitoneally to the mice in the MSC administration group. To the mice in the control group, 100 µl of PBS was administered intraperitoneally on the 5th day of DSS drinking. No substance was administered to the normal mice (n=3).
iii) Evaluation of the Effect of Mesenchymal Stem Cell Administration The body weight of the mice was measured daily until the 9th day after the start of drinking the DSS aqueous solution.
(2) Results FIG. 9 shows the change in body weight of the mice during the test period (see "Water" for the normal mice, "DSS+PBS" for the control group, and "DSS+MSCs" for the MSC administration group). The body weight of the IBD model mice (in the control group and the MSC administration group) decreased as the days passed. There was no difference in the body weight change between the MSC administration group and the control group, and the improvement effect of MSC administration was not observed.

Under the conditions of this comparative example, the administration of mesenchymal stem cells did not suppress weight loss of the inflammatory bowel disease model mice. However, the HMGB1 peptide (1-44) showed an effect of ameliorating symptoms such as weight loss in the inflammatory bowel disease model mice produced under the same conditions as the above. From this, it is expected that the peptide of the present application will also be effective for patients with inflammatory bowel diseases who cannot obtain an effect from the administration of mesenchymal stem cells.

INDUSTRIAL APPLICABILITY

Pharmaceutical compositions comprising the peptide of the present application are expected to provide great benefits to patients with inflammatory bowel diseases who cannot obtain a sufficient effect with existing therapeutics.

The invention claimed is:

1. A method of treating an inflammatory bowel disease, comprising administering to a subject with the inflammatory bowel disease an effective amount of a substance described in any of following (a) to (b):

(a) a peptide consisting of the amino acid sequence described in SEQ ID NO: 1; and (b) a peptide consisting of an amino acid sequence having 95% or more sequence identity with the amino acid sequence described in SEQ ID NO: 1.

2. The method of claim 1, wherein the inflammatory bowel disease is a non-specific inflammatory bowel disease.

3. The method of claim 2, wherein the non-specific inflammatory bowel disease is ulcerative colitis.

4. The method of claim 2, wherein the non-specific inflammatory bowel disease is Crohn's disease.

5. A method of suppressing weight loss or intestinal mucosal damage in a patient with an inflammatory bowel disease, comprising administering to the patient an effective amount of substance described in any of following (a) to (b):
   (a) a peptide consisting of the amino acid sequence described in SEQ ID NO: 1;
   (b) a peptide consisting of an amino acid sequence having 95% or more sequence identity with the amino acid sequence described in SEQ ID NO: 1.

6. The method of claim 5, wherein the inflammatory bowel disease is a non-specific inflammatory bowel disease.

\* \* \* \* \*